United States Patent
Kasano

(10) Patent No.: US 6,622,037 B2
(45) Date of Patent: Sep. 16, 2003

(54) TRANSDERMAL ADMINISTRATING DEVICE

(75) Inventor: Hiroyuki Kasano, Kanazawa (JP)

(73) Assignee: Polytronics, Ltd., Kanazawa (JP)

( * ) Notice: Subject to any disclaimer, the term of this patent is extended or adjusted under 35 U.S.C. 154(b) by 4 days.

(21) Appl. No.: 09/825,007

(22) Filed: Apr. 3, 2001

(65) Prior Publication Data

US 2001/0029347 A1 Oct. 11, 2001

(30) Foreign Application Priority Data

Apr. 5, 2000 (JP) .................................. 2000-103298

(51) Int. Cl.$^7$ ................................................ A61N 1/30
(52) U.S. Cl. ......................................................... 604/20
(58) Field of Search .......................... 604/20, 289, 290, 604/501; 607/149, 115

(56) References Cited

U.S. PATENT DOCUMENTS

| | | | | |
|---|---|---|---|---|
| 5,746,711 A | * | 5/1998 | Sibalis et al. .................. | 604/20 |
| 6,035,234 A | * | 3/2000 | Riddle et al. .................. | 604/20 |
| 6,086,572 A | * | 7/2000 | Johnson et al. ............... | 604/503 |
| 6,175,763 B1 | * | 1/2001 | Sorenson et al. .............. | 604/20 |
| 6,295,469 B1 | * | 9/2001 | Linkwitz et al. ............... | 604/20 |
| 6,326,160 B1 | * | 12/2001 | Dunn et al. .................... | 435/14 |

FOREIGN PATENT DOCUMENTS

| | | |
|---|---|---|
| DE | 40 28 125 A1 | 7/1991 |
| EP | 0 788 810 A3 | 8/1997 |
| EP | 0 788 810 A2 | 8/1997 |
| EP | 0 815 899 A1 | 1/1998 |
| JP | 10-118041 A | 5/1998 |
| WO | WO 99/30773 A | 6/1999 |

OTHER PUBLICATIONS

Patent Abstracts of Japan, vol. 1998, No. 10, Aug. 31, 1998 and JP 10–118041 A (Poritoronikusu: KK) May 12, 1998—Abstract; Figs. 1, 2.

* cited by examiner

*Primary Examiner*—Sharon Kennedy
(74) *Attorney, Agent, or Firm*—Frishauf, Holtz, Goodman & Chick, P.C.

(57) ABSTRACT

A transdermal administrating device is provided which includes an active electrode having a conductive electrode layer and a conductive drug layer applied on the bottom surface of the conductive electrode layer. The bottom surface of the conductive drug layer is capable of being placed in contact with skin. The device also includes an inert electrode capable of being placed in contact with skin and spaced from the active electrode, a set of conductive electrode layers each having a different standard single electrode potential, and a controller for measuring an internal resistance of the skin tissue under the region between the conductive electrode layers and for controlling an electric current passing between the active electrode and the inert electrode based on the variation in the internal resistance. In addition, a dermocontact mechanism is provided for keeping the active electrode, the inert electrode, and the set of conductive electrode layers in contact with skin.

20 Claims, 14 Drawing Sheets

TRANSDERMAL ADMINISTRATING DEVICE

This application is based on Japanese Patent Applications 2000-103298 filed on Apr. 5, 2000, the entire contents of which is incorporated herein by reference.

BACKGROUND OF THE INVENTION

1. Field of the Invention

The present invention relates to a transdermal administrating device, and more particularly, to a transdermal administrating device which allows an ionic agent to permeate from a predetermined site on the surface of skin into subcutaneous tissue by using the principle of iontophoresis.

2. Description of the Related Art

Iontophoresis is a transdermal drug delivery technique which permits drug ions to permeate into subcutaneous tissue while drifting them under a potential applied on a skin medium by using electrophoretic phenomenon.

For example, a set of electrodes are placed being in contact with the surface of skin and spaced from each other.

One of the electrodes of the set is called an active electrode. The active electrode contains a conductive electrode layer and a conductive matrix layer, i.e., a drug reserving and releasing layer (which is referred to as a conductive drug layer hereinafter) having dispersed ionic drug(s) which is applied on one surface of the conductive electrode layer.

The active electrode should be disposed in such a manner as the conductive drug layer is in contact with skin.

The other electrode has usually no conductive drug layer on the bottom surface thereof. This electrode is referred to as an inert electrode.

In the present specification, such a condition as the electrode or the conductive drug layer being placed in contact with skin is referred to as "dermocontact".

A power supply is connected between the active electrode and the inert electrode. Polarity of the power supply to be connected to each of the electrodes is selected so that the drug ions are drifted from the active electrode to the inert electrode in the subcutaneous tissue. Application of power between the electrodes produce an electric field in the non-dermocontact region of the subcutaneous tissue and the field allows the drug ions contained in the conductive drug layer disposed in the active electrode to be withdrawn into the subcutaneous tissue. The drug ions withdrawn into the subcutaneous tissue may enter into, e.g. blood vessels.

The transdermal drug delivery process by iontophoresis makes it possible to miniaturize a drug dispenser itself as opposed to the conventional administrating processes such as ordinary dropping. Miniaturization of devices permits patients to carry them, thereby reducing a load in daily life.

The transdermal drug delivery process by iontophoresis can reduce a burden to patients and enhance a quality of life of patients. Therefore, it is an excellent drug delivery system. The power supply may be a small dry battery based on portability.

Drugs having a narrow acceptable range of drug concentration, such as hormone drug, anti-cancer drugs, anaesthetics and the like are administrated into a blood vessel by venous penetration. In this case, the drug-concentration in blood is controlled by monitoring a dosage amount into a blood vessel to adjust the dropping rate of the drug(s).

If iontophoreisis, which is a non-invasive drug delivery method, is employed, it is difficult to appropriately monitor the amount of drug to be dispensed into blood vessels. Therefore, iontophresis has been less applicable to administration of drugs having a narrow acceptable range of blood drug-concentration.

SUMMARY OF THE INVENTION

An object of the present invention is to provide a novel transdermal drug delivery technique, which can be applied to administration of various drugs including those having a narrow acceptable range of blood drug concentration in blood.

According to an aspect of the present invention, there is provided a transdermal administrating device comprising; an active electrode having a conductive electrode layer and a conductive drug layer applied on one surface of said conductive electrode layer, said conductive drug layer being placed in contact with skin; an inert electrode made of electro conductive material which is placed in contact with skin and spaced a distance from said active electrode; a means of applying a variable voltage across said active electrode and said inert electrode; a set of first and second conductive electrode layers, each made of a material having a different standard single electrode potential, which are placed in contact with skin and spaced a distance from each other; a controller connected to a non-dermocontact region between said first conductive electrode layer and said second conductive electrode layer and measuring an internal resistance of subcutaneous tissue between said first electrode layer and said second electrode layer and controlling an electric current passing through the subcutaneous tissue between said active electrode and said inert electrode based on the measured internal resistance; and a dermocontact means for keeping said active electrode, said inert electrode, and said first and second electrodes in contact with skin.

According to another aspect of the present invention, there is provided a process for drug delivery comprising steps consisting of (a) attaching on the surface of skin an active electrode having a conductive electrode layer and a conductive drug layer applied on one surface of said conductive electrode layer, said conductive drug layer being placed in contact with skin; an inert conductive electrode which is placed in contact with skin and spaced a distance from said active electrode; and a set of first and second conductive electrode layers, each made of a material having a different standard single electrode potential, which are placed in contact with skin and spaced a distance from each other, (b) detecting an electric current passing through an subcutaneous tissue between said first conductive electrode layer and said second conductive electrode layer to evaluate an internal resistance of the subcutaneous tissue, (c) determining an internal resistance for keeping a concentration of the drug ions in blood at a desired level based on a predetermined calibration curve which shows a relationship between the concentration of the drug ions released from said conductive drug layer and the internal resistance, and (d) controlling said electric current passing through the subcutaneous tissue between said active electrode and said inert electrode so as to maintain said internal resistance obtained in the step (c).

Iontophoresis can be carried out by placing both the conductive drug layer attached intimately on the bottom surface of the active electrode and the inert electrode in contact with skin apart from each other and applying a monopolar potential in the non-dermocontact region between the active electrode and the inert electrode to cause a drift of the effective drug component(s) from the conductive drug layer into the subcutaneous tissue. A chemical cell is formed among a skin and the electrodes when simultaneously the positive electrode and the negative electrode, each made of a conductive material having a different standard single electrode potential, are separately placed in contact with skin. Then, by measuring and calculating a variation in an internal loss of the chemical cell, a variation in the concentration of the effective component(s) permeated into the subcutaneous tissue can be obtained. This result is fed back to the control of the single electrode potential or the flowing current so as to control the drug concentration in blood.

For iontophoresis, the active electrode and the inert electrode are used. For the detection of the internal loss of the chemical cell, a set of the first conductive electrode layer and the second conductive electrode layer each made of an electrically conductive material having a different standard single electrode potential is used as a sensor. The active electrode and the inert electrode may be served as a set of conductive electrode layers, too.

In order to maintain the chemical stability of the surface of electrode, there may be employed an device structure where the dermocontact sides of the inert electrode and (or) the drug-contact side of the active electrode are coated with materials different from those of the inert electrode and the active electrode.

It is possible to control the monopolar potential applied across the active electrode and the inert electrode by the DC power supply in connect with the non-dermocontact region between the active electrode and the inert electrode, which power supply is for applying a bias voltage. Alternatively, the control of the flowing current may be achieved by controlling the value of an electric resistance interposed between the active electrode and the inert electrode.

It is contemplated to use a combination of two electrically conductive materials having different single electrode potentials where among them, the one having a lower single electrode potential may be of n-type semiconductor. Employing the n-type semiconductor negative electrode can sustain stably the electrode reaction because a Schottky potential barrier formed on the dermocontact surface prevents anions from invading into the negative electrode. In addition, the hole injection from the negative electrode into the subcutaneous tissue reduces alkalization of the skin resulting in an reduction in skin damage.

The present invention makes advantageously it possible to control easily the drug concentration in blood, to enhance the quality of life of patients, and moreover to add to a variety of transdermally administrable drugs.

BRIEF DESCRIPTION OF THE DRAWINGS

FIG. 1A is a schematic view of the transdermal administrating device. FIG. 1B is for describing actual operation of the transdermal administrating device showing an arrangement of external load.

FIG. 1C shows an equivalent circuit of the arrangement shown in FIG. 1B. FIG. 1D shows a more simplified equivalent circuit similar to that shown in FIG. 1C.

FIG. 2A shows an arrangement of the transdermal administrating device without requiring a bias power supply. FIG. 2B shows an arrangement of the device where CPU contains a power supply with requiring a bias power supply. FIG. 2C shows an arrangement where an external power supply provided separately is used as a power supply for CPU.

FIG. 3A is a plane view of the transdermal administrating device. FIG. 3B is a cross-sectional view of the device taken along the IIIa–IIIb line in FIG. 3A. FIG. 3C shows specifically an detailed arrangement of the external resistor in the arrangement shown in FIG. 3B.

FIG. 7A is a plane view of the dermocontact side of the transdermal administrating device. FIG. 7B is a cross-sectional view of the device taken along the VIIa–VIIb line in FIG. 7A and interconnections among electric circuit elements which are provided on the back of the dermocontact side.

FIG. 10A is a plane view of the dermocontact side of the transdermal administrating device. FIG. 10B is a cross-sectional view of the device taken along the Xa–Xb line in FIG. 10A and interconnections among electric circuit elements which are provided on the back of the dermocontact side.

FIG. 11A is a plane view of the dermocontact side of the transdermal administrating device.

FIG. 11B is a cross-sectional view of the device taken along the XIa–XIb line in FIG. 11A and interconnections among electric circuit elements which are provided on the back of the dermocontact side.

FIG. 12A is a plane view of the dermocontact side of the transdermal administrating device. FIG. 12B is a cross-sectional view of the device taken along the XIIa–XIIb line in FIG. 12A and interconnections among electric circuit elements which are provided on the back of the dermocontact side.

DETAILED DESCRIPTION OF PREFERRED EMBODIMENTS

Figure 1A:
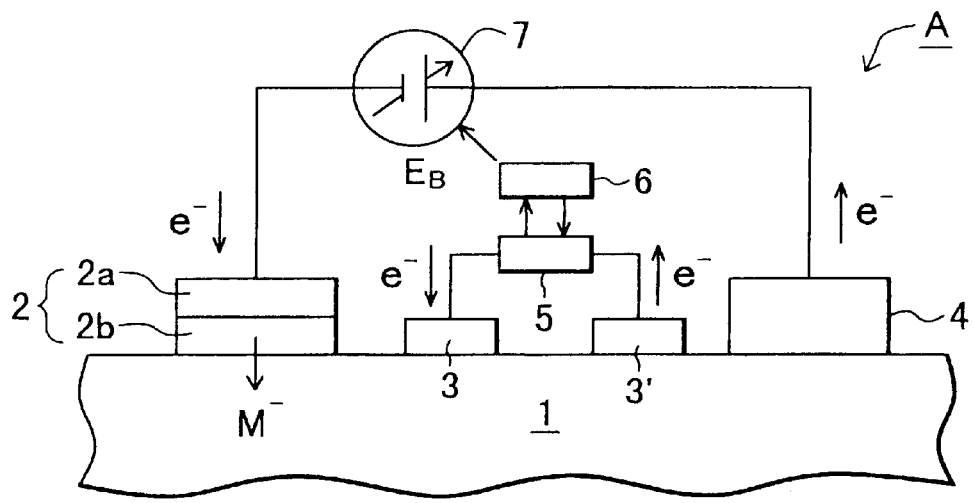
FIGS. 1A and 1B are for describing the principle of the transdermal administrating device according to the present invention.

Before embodiments of the present invention are described, the related art is first described under.

The iontophoresis process is widely used for administration of agents which are difficult to permeate into the subcutaneous tissue only by spreading on the skin, such as non-invasive administration of macromolecular agents.

The agents, which may be used by the iontophoresis, include a variety of drugs such as peptide, β-blocker, insulin, calcitonin, morphine as well as anti-inflammatory drugs. There are many drugs which are obscure in their permeation route and the like.

The transdermal drug delivery is excellent in quantitative control of drugs in blood and local administration of the drugs. It is applicable to a variety of drugs. In order to put the iontophoresis process capable of administrating macromolecular high molecular weight agents into practice, it is necessary to confirm both a reduction in cost and safety.

The present inventors have developed a drug delivery device, i.e., a biocell type administration device, which is essentially excellent in view of reduction in delivery cost and secured safety for iontophoresis. The biocell type administration device employs two types of materials having different standard single electrode potentials for a conductive electrode of an active electrode and for an inert electrode.

A pair of a metal having a higher standard single electrode potential and a n-type semiconductor having a lower standard single electrode potential may be used. The metal electrode having a higher standard single electrode potential will be a positive electrode. The subcutaneous tissue acts as electrolyte. The n-type semiconductor will be a negative electrode.

There is formed a chemical cell with the metal electrode having a higher standard single electrode potential (positive electrode) and the n-type semiconductor having a lower standard single electrode potential (negative electrode) and the subcutaneous tissue.

The use of a DC electromotive force generated by electrically interconnecting the positive electrode and the negative electrode at a non-dermocontact region, permits iontophoresis to occur in the subcutaneous tissue between the two electrodes.

The skin forms a current path through the chemical cell between the active electrode and the inert electrode. When the positive electrode and the negative electrode are in short due to perspiration and the like, the redox reactions on the skin cease and the electromotive force of the cell disappears. Therefore, dangerous accidents such as skin damage (burn) attributable to generation of excess current can be avoided. Moreover, when a current is flowing, holes are injected from the negative electrode in the subcutaneous tissue so that a phenomenon of alkalization of the skin under the negative electrode is reduced.

As is described, the above-mentioned transdermal administrating device is excellent in safety. Because of requiring no external power supply, it can be easily made to be dispersible, and reduced in production cost.

The iontophoresis technique is for administrating ionic drug(s) from the surface of skin into a living body by using field acceleration. If the concentration of the drug(s) is uniformly dispersed throughout the conductive drug layer is uniform, the concentration of the drug(s) to be administrated is proportional to the field strength, the current density and the dermocontact area of the drug layer while flowing a current.

The concentration of drug(s) in the subcutaneous tissue after administration (subcutaneous concentration) is largely dependent upon personal difference and the elapsed time. Therefore, it is difficult to maintain the subcutaneous drug concentration consistently at a constant value.

Of course, even by other methods such as oral administration or injection, it is more difficult to maintain the drug concentration in blood at a predetermined level. Generally the administration of drug(s) is adjusted in such a manner that the concentration level in blood is in the range from the minimum requisite concentration to the maximum acceptable one.

In the iontophoresis process, i.e., the non-invasive administration process, it is difficult to observe the concentration of the drug transdermally permeated into the subcutaneous tissue with time. Therefore, it has been considered that iontophoresis is not suitable for administration of such a drug as having a narrow acceptable concentration zone. In addition, from an essential standpoint of iontophoresis to improve the quality of life of patients, it is not preferably to employ a procedure of monitoring and controlling the amount of a drug permeated into blood vessels by using invasive concentration-meter.

In view of the foregoing, the present inventor made the following consideration.

If it is possible to control non-invasively the concentration of administrated drug(s) with time by using the iontophoresis process, a device for transdermal administration of drugs using this principle can be used for administration of a wide variety of drugs including those having a narrow acceptable range of the drug-concentration in blood.

If it is possible to measure non-invasively the subcutaneous concentration of drugs with time and then feed back the measurements to a bias voltage or flowing current between the active electrode and the inert electrode to control the concentration, the drug-concentration in blood can be kept constant.

The present inventors have previously clarified that an internal loss of a chemical cell made of skin electrolyte and a pair of electrodes disposed on the surface of skin, i.e., a metal electrode having a higher standard single electrode potential and a semiconductor electrode having a lower standard single electrode potential, is intimately correlated with a physiological activities of skin and subcutaneous tissue, and developed a technique capable of measuring non-invasively the internal loss with excluding an influence of skin resistance (Japanese Patent Application No. Hei 8-284295).

Figure 1B:
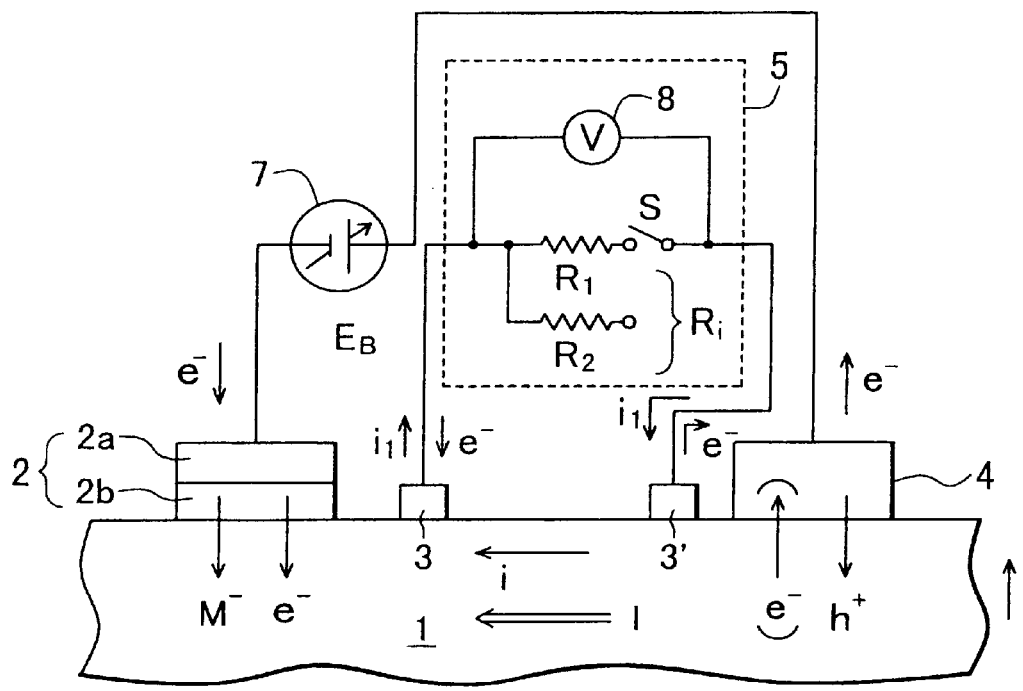
Figure 1C:
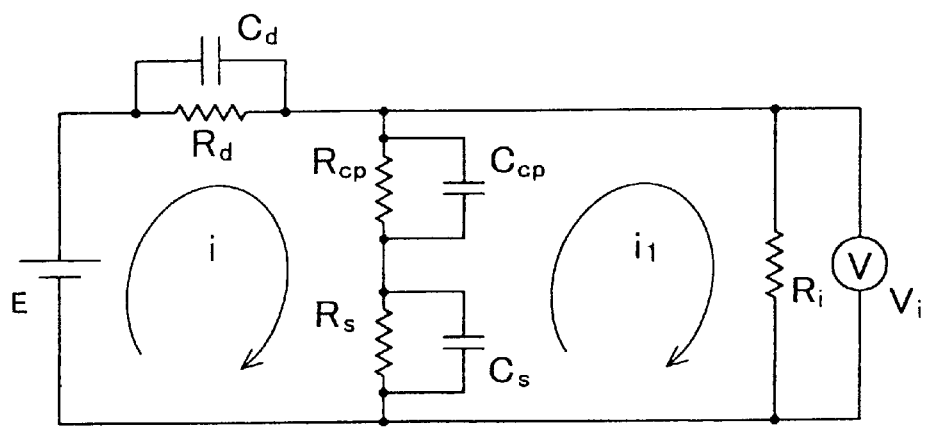
FIGS. 1C and 1D are for describing the principle of the transdermal administrating device according to the present invention.
Figure 1D:
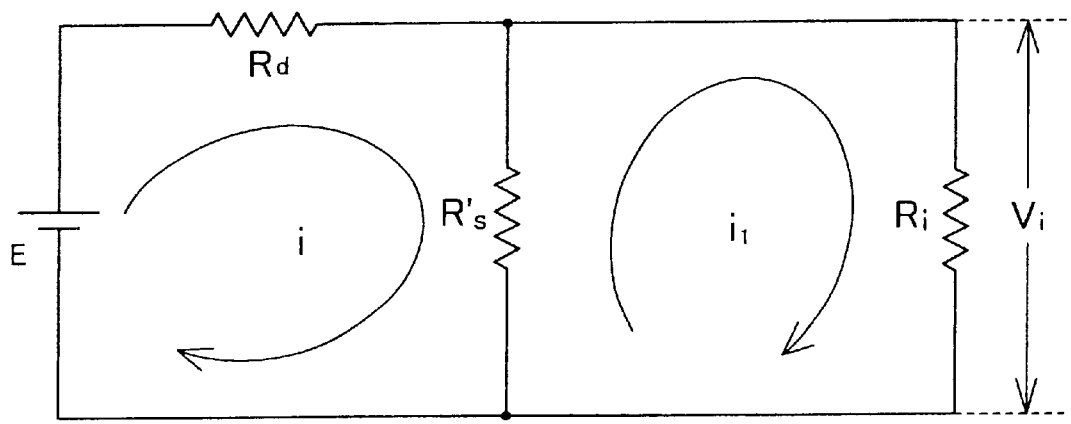

FIGS. 1A to 1D are a schematic view showing the principle of the transdermal administrating device according to the present invention. FIG. 1A show a general arrangement of the device. FIG. 1B shows in more detail an arrangement of a detection part for measuring a variation in drug concentration. FIG. 1C shows an equivalent circuit of an electric components formed by the detection part of the transdermal administrating device and skin. FIG. 1D shows a more simplified equivalent circuit similar to that shown in FIG. 1C.

As shown in FIGS. 1A and 1B, in the transdermal administrating device A, an active electrode 2 containing a conductive electrode layer 2a and a conductive drug layer 2b forms a counterpart to an inert electrode 4. The active electrode and the inert electrode are placed in contact with the surface of skin 1 and spaced a distance from each other.

A bias DC power supply (voltage $E_B$) 7 is connected to the active electrode 2 and the inert electrode 4. On the other hand, as a sensor of the detection part, the first and the second conductive electrode layers 3, 3' of the set are placed in contact with the surface of skin 1 spacing from each other in the vicinity of the active electrode 2 and the inert electrode 4. The set of the conductive electrodes 3, 3' is connected to an external load 5 under non-dermocontact condition. The external load 5 and the bias DC power supply 7 are connected to CPU 6.

Informations are transmitted between the CPU 6 and the external load 5 as shown by arrows. The bias power supply 7 can vary a voltage to be applied to the electrodes according to the instructions from the CPU 6 as shown by an arrow.

The CPU 6 may be directly connected or not connected to the external load 5 or the bias power supply 7. For example, it may be constructed so that it can instruct the bias power supply 7 to apply a bias voltage to the electrodes 2, 4 by a remote control.

FIGS. 1 and 2 illustrate a case where an effective drug component is anionic ($M^-$). If the effective drug component is cationic, the bias power supply 7 is only required to be inversely connected to the active electrode and the inert electrode. The standard single electrode potential of the conductive material for each of the first and the second conductive electrode layers 3, 3' is selected to be different from each other. In FIG. 1A, the standard single electrode potential of the material for the first conductive electrode layer 3 is higher than that for the second conductive electrode layer 3'.

Description will be made with reference to a case where the effective drug component is anionic hereunder.

Generally the first conductive electrode layer 3 is made of metal and the second conductive electrode layer is made of metal or semiconductor. The first and the second conductive electrode layers 3, 3' are placed apart from each other to be in contact with the surface of skin.

The external load 5 is disposed between the first and the second conductive electrode layers 3, 3', which forms an electric closed circuit with the skin tissue 1. That is, a chemical cell with the skin tissue as an electrolyte is formed. The electromotive force of this cell causes a current i to flow along the closed circuit in the direction as shown in FIG. 1B by arrows. Electrons ($e^-$) flow from the second conductive electrode layer having a lower standard single electrode potential 3' through the external load 5 to the first conductive electrode layer 3 having a higher standard single electrode potential.

On the other hand, in the circuit for the iontophoresis, the bias power supply 7 biases the conductive electrode layer 2a to cause electrons ($e^-$) therefrom to enter into the conductive drug layer 2b coated on the bottom surface of the layer 2a. The electrons forces the $M^-$ anions contained in the conductive drug layer 2b to be released therefrom into the subcutaneous tissue. A part of the electrons enter into the subcutaneous tissue with the $M^-$ ions. The remaining electrons corresponding to the amount of the $M^-$ ions transferred into the subcutaneous tissue react with cations in the conductive drug layer 2 to disappear.

When the inert electrode 4 is made of metal, electrons are supplied from the subcutaneous tissue to the inert electrode 4 after it released electrons to the active electrode 2 through a wiring. When the inert electrode 4 is made of n-type semiconductor, excess holes are released into the tissue to compensate for the lack of electric neutrality, which is caused by the electron releasing into the active electrode 2. The electrons entered into the subcutaneous tissue in a region in contact with the bottom surface of the conductive drug layer 2b produce a reducing with cations existing in the subcutaneous tissue.

On the other hand, in the subcutaneous tissue region in contact with the bottom surface of the inert electrode 4, an oxidation reaction is caused. When the inert electrode 4 is of metal, there is caused a reaction to produce electrons, while when the inert electrode 4 is of n-type semiconductor, there is caused an oxidation reaction with injected holes.

As shown in the square surrounded with dotted lines in FIG. 1B, the external load 5 contains standard resistors $R_i$ (i=1, 2), a potentiometer V and a switch (electronic switch) S in a circuit. By operation of the switch S one can select which of the two standard resistor $R_1$ or $R_2$ should be connected between the first and the second pairs of conductive electrode 3, 3'.

When a variation in the concentration of drug(s) in the subcutaneous tissue is to be detected, the two standard resistors are sequentially switched from one to the other as $R_1 \rightarrow R_2$ in a short time (about 0.01 second) with measuring a voltage drop between both ends of the standard resistor $V_i$(i=1, 2) by the potentiometer 8 at every switching.

The switching of the standard resistor can be performed by the electronic switch S according to the instruction of CPU 6.

FIG. 1C shows an equivalent circuit of the detection part containing the skin tissue, in which $R_d$ represents a resistance to an electric current flowing within skin tissue 1, Cd represents a capacity and E represents a DC electromotive force of the chemical cell with the skin tissue 1 as electrolyte.

The DC electromotive force E of the chemical cell depends upon the difference in standard single electrode potential between the first and the second conductive electrode 3, 3' (the magnitude of electronic current density to be flowable through the circuit per unit time). The higher the difference in standard single electrode potential, the larger the electronic current density to be flowable through the circuit per unit time is. Therefore, the electromotive force E can be unequivocally determined by the characteristics of the materials forming the first and the second conductive electrode 3, 3'.

The electrons injected from the conductive electrode having a higher standard single electrode potential 3 into the skin tissue 1 causes a reducing reaction with cations distributed within the skin tissue. In the tissue region under the second conductive electrode having a lower standard single electrode potential 3' there is produced an oxidation reaction. As a result, an ionic current i flows inside the skin tissue 1 as shown in FIGS. 1B and 1C.

Simply non-invasive pressing of the first and the second conductive electrode layers 3, 3' onto the skin 1 may produce a high contact impedance between both electrode layers and the skin. There are impedance components perpendicular to the surface of skin $R_{cv}$ and that parallel to the surface of skin $R_{cp}$. $R_{cp} \gg R_{cv}$. Therefore, the $R_{cv}$ may be negligible. There is a leakage current flowing on the surface of skin between the first conductive electrode layer 3 and the second conductive electrode layer 3'. The leakage resistance is designated as $R_s$, and the capacitance as Cs.

The time constant of the skin impedance as shown in FIG. 1C was measured to be larger than 0.1 second. Therefore, the external load resistance $R_i$=1, 2 are switched in such a time interval as charge and discharge of capacitances, $C_d$, $C_{cp}$, and $C_s$ being negligible, for example, within not more than 0.01 second with measuring $V_i$ at every switching.

If the charge and discharge of capacitances $C_d$, $C_{cp}$ and $C_s$ can be ignored, the circuit of FIG. 1C may be approximately simplified into the equivalent circuit as shown in FIG. 1D.

Here, with $$R_{cp} + R_s = R_s' \text{ and } R_i = R_1, V_i = V_0,$$

then, applying Kirchhiff's law to the closed circuit as shown in FIG. 1D gives the following equations:

$$R_d i + R_s'(i - i_1) = E \quad [1]$$

$$R_s'(i_1 - i) + R_1 i_1 = 0 \quad [2]$$

$$R_1 i_1 = V_1 \quad [3]$$

From the above equations [1] and [2], i is eliminated:

$$i_1 = R_s' E / (R_s' R_d + R_d R_1 + R_1 R_s')$$

Elimination of $i_1$ gives the following equation:

$$R_s' \{R_1 E - (R_d + R_1) V_1\} = R_d R_1 V_1 \quad [4]$$

Next, a closed circuit shown in FIG. 1D where $R_i$ is changed from $R_1$ to $R_2$ is considered.

Changing currents flowing each closed circuit, i to i'; $i_1$ to $i_2$; and $V_1$ to $V_2$, then equations [1'] to [3'] corresponding to [1] to [3], respectively:

$$R_d i' + R_s'(i' - i_2) = E \quad [1']$$

$$R_s'(i_2 - i') + R_2 i_2 = 0 \quad [2']$$

$$R_2 i_2 = V_2 \quad [3']$$

From equation [3'], $i_2 = V_2/R_2$

If i' and $i_2$ are eliminated from above equations [1'] to [3'], the following equation can be obtained:

$$R_s' \{R_2 E - (R_d + R_2) V_2\} = R_d R_2 V_2 \quad [4']$$

The i and the i' are different from each other. However, if $R_i$ is switched from $R_1$ to $R_2$ in a very short time and $V_1$ and $V_2$ are measured, $R_d$ and $R_s'$ may be deemed to be substantially the same with $R_1$ and $R_2$ inserted, respectively.

Therefore, from the equations [4] and [4'], the following equation can be produced:

$$R_1 V_1 \{R_2 E - (R_d + R_2) V_2\} = R_2 V_2 \{R_1 E - (R_d + R_1) V_1\}$$

Resulting in $$R_d = R_1 R_2 E (V_1 - V_2) / V_1 V_2 (R_1 - R_2) \quad (1)$$

In short, a variation in current when $R_i$ is switched from $R_1$ to $R_2$ can be determined by measuring $V_1$ and $V_2$. Excluding influences of the contact resistance which is liable to vary with time and due to personal difference and of leak current, a variation in the resistance inside the skin tissue 1 between the two electrodes is measured at regular intervals, whereby the internal loss factor $R_d$ of the biocell can be estimated by using the equation (1).

When the device as shown in FIGS. 1A and 1B is used to allow the effective drug component $M^-$ to permeate into the subcutaneous tissue, $R_d$ is largely influenced by the concentration of $M^-$ ions in the subcutaneous region, $[M^-]_1$ and given as a function of $[M^-]_1$.

That is, $R_d = F([M^-]_1)$. When the subcutaneous concentration of $M^-$ ions $[M^-]_1$ reaches almost at a constant level after a transient period has elapsed, the concentration of $M^-$ is much higher by orders of magnitude than those of other various ions in the same region of the vicinity of the area of the active electrode 2. As a result, in many cases, $R_d$ may be inversely proportional to the concentration of $M^-$ ions.

Therefore, the drug ion concentration can be controlled by monitoring the $R_d$ expressed by the equation (1).

The subcutaneous concentration of $M^-$ ion $[M^-]_1$ and the concentration of $M^-$ ion in blood $[M^-]$ have a constant interrelation with each other. Therefore, it is possible to control the blood drug concentration in blood $[M^-]$ by controlling the subcutaneous concentration of ions. The device as shown in FIG. 1A is operated for controlling the drug concentration in blood as follows:

Based on the measurements as described above, the data of $R_i$ and $V_i$ of the external load 5 are transmitted to CPU 6. The CPU 6 calculates $R_d$ based on the above equation (1). If the drug ion concentration in blood $[M^-]$ is lower than a target value, in other words, the value of $R_d$ is higher than a predetermined one, the information permits the bias voltage $E_B$ of the bias power supply to rise so that the $R_d$ approaches the predetermined value.

Conversely, if the $[M^-]$ is higher than the target value, the $E_B$ is lowered.

As can be seen from FIG. 1A, the active electrode 2 and the inert electrode 4 have a function of forcing the subcutaneous permeation of drug ions $M^-$ (a bias function). A set of the first and the second conductive electrode 3, 3' disposed near the active electrode and the inert electrode has a function of sensing the subcutaneous ion concentration (a sensor function).

In the aforementioned embodiment, description has been made about arrangements where the iontophoresis circuit and the detection circuit are separately formed as shown in FIGS. 1A and 1B. When the internal resistance is not detected, the switch S may be turned off [FIG. 1B].

Alternatively, the active electrode and the inert electrode may act also as electrodes for detecting internal resistance (a set of the first and the second conductive electrode layer 3, 3'). This arrangement will be described in detail in Example 1 or under. For example, in the case of FIGS. 3A to 3C, iontophoresis may be performed by flowing a current with the resistance $R_1$ or $R_0$ inserted in the external circuit as a resistances for protecting the power supply circuit for iontophoresis. It is possible to protecting the circuit by providing resistances other than $R_1$ or $R_0$.

As described above, in this case, the sensor electrodes are composed of two sorts of materials having different standard single electrode potentials. However, preferably the bias electrodes, namely the conductive electrode 2a of he active electrode and the inert electrode 4, should be made of the same material from the standpoint of production cost.

In order to simplify the device structure, an electrode arrangement having these two functions may be made. The conductive electrode layer 2a of the active electrode and the inert electrode 4 may be made of materials having different standard single electrode potentials from each other. In this case, iontophoresis and the detection of the concentration of drug ions may be carried out even without using the bias power supply 7 ($E_B$=0) because the biocell can work, as is shown in FIG. 2.

Generally a four-electrode scheme where the aforementioned two functions are separated from each other may be desired from the standpoint of the operability of the devices. However, a two electrode scheme as shown in FIG. 2 is more desired from the point of view of cost. As an intermediate scheme therebetween, a three-electrode scheme may be used where at least the inert electrode is used as one of the sensor electrodes, as is shown in FIG. 3.

The equivalent circuit in this case has a configuration of FIG. 1C and FIG. 1D where an $E_B$ is inserted in the closed circuit with flowing current $i_1$ since the bias DC power supply 7 is used. Application of Kirchhoffs law to this equivalent circuit similarly to the previous case gives the following equation:

$$R_d = R_1 R_2 E(V_1 - V_2) / \{V_1 V_2 (R_1 - R_2) + E_B(V_1 R_2 - V_2 R_1)\} \quad (2)$$

As can be clearly seen from the equations (1) and (2), if E=0, i.e., a pair of electrodes having a sensor function are made of materials having the same standard single electrode potential, a non-invasive control of the $M^-$ ion concentration in blood [$M^-$] can not be achieved even when the bias DC power supply 7 flows a current I through the subcutaneous tissue, because of $R_d$=0.

In contrast, the two-electrode scheme makes it possible to detect $R_d$ even without using the bias DC power supply ($E_B$=0) when a pair of electrodes has different standard single electrode potentials.

Figure 2A:
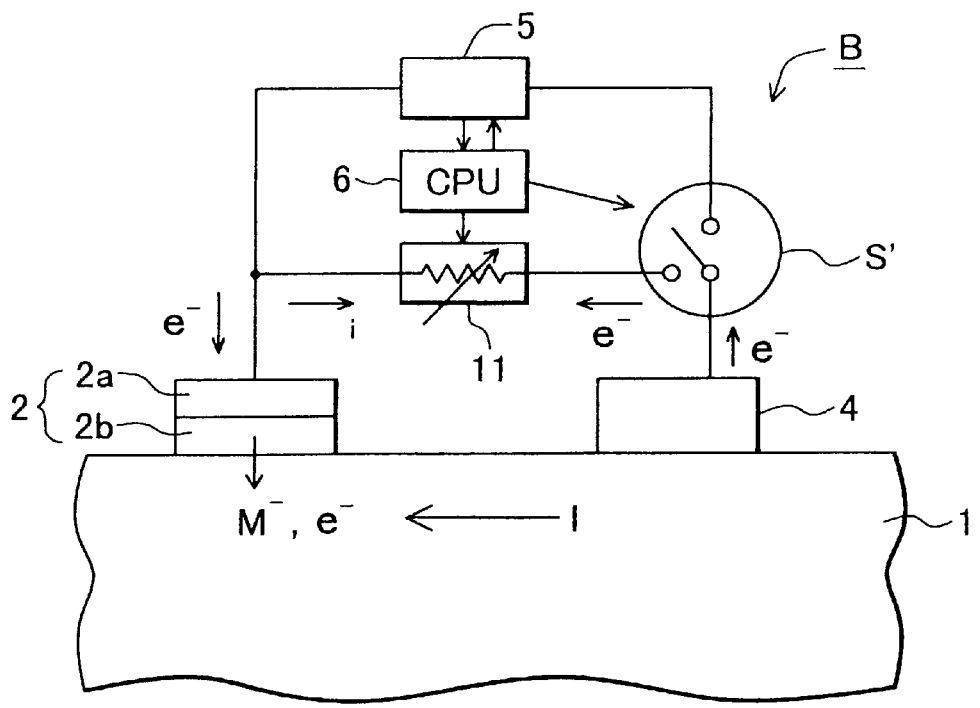
FIGS. 2A, 2B, and 2C are for describing the principle of the transdermal administrating device according to the present invention.

When the bias DC power supply 7 is not used, as shown in FIG. 2A, the $R_d$ calculated by the CPU 6 is fed back to a variable element in place of the bias DC power supply 7, for example, a variable resistor or a current varying element so as to control the circuit current, thereby controlling the concentration of $M^-$ions to be permeated into subcutaneous tissue.

Figure 2B:
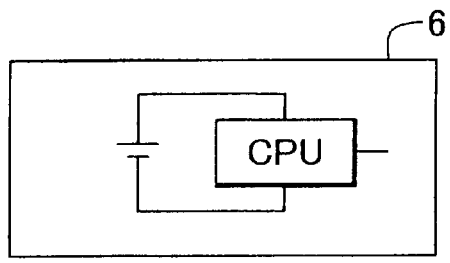
Figure 2C:
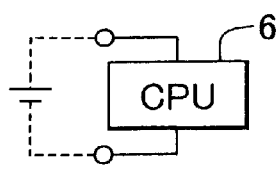

By using the two electrode scheme, i.e., the active electrode and the inert electrode, the $R_d$ may be monitored in the transdermal administrating device without the bias DC power supply, as described under with reference to FIG. 2A to FIG. 2C.

The transdermal administrating device B, as shown in FIG. 2A, comprises an active electrode 2 containing a conductive electrode layer 2a and a conductive drug layer 2b (to be placed in contact with the skin tissue 1) applied on the bottom surface of the conductive electrode layer and an inert electrode 4 (to be placed in contact with the skin and spaced from the active electrode 2), an external load 5, CPU 6, a variable resistor 11 and an electronic switch S'.

The external resistor 5 and the variable resistor 11 are parallelly arranged between the active electrode 2 and the inert electrode 4.

By operation of the electronic switch S', one can select which of the external resistor 5 or the variable resistor 11 should be connected between the active electrode 2 and the inert electrode 4. If the external resistor 5 is connected between the active electrode 2 and the inert electrode 4, a $R_d$ detection circuit is formed. In contrast, if the variable resistor 11 is connected between the active electrode 2 and the inert electrode 4, an iontophoresis circuit is formed for administrating drug(s) into the subcutaneous tissue.

The CPU 6 instructs the electronic switch S' to change from the iontophoresis circuit to the $R_d$ detection circuit at constant intervals so as to measure the voltages $V_1$ and $V_2$. The $R_d$ is calculated by using the equation (1).

Again in this case, it is necessary to prepare a calibration line by previously determining a relationship between the $R_d$ and the blood drug ion concentration in blood [$M^-$]. A standard internal resistance $R_{d0}$ is predetermined corresponding to the desired concentration of drug ions based on the calibration line. Comparing with the detected internal resistance $R_d$ and the standard internal resistance $R_{d0}$, the value of the variable resistor 11 is controlled so that the internal resistance approaches the standard internal resistance with varying the flowing current I. That is, by varying the value of the variable resistance 11 is varied to control the blood drug ion concentration in blood [$M^-$] is controlled. In the circuit shown in FIG. 2A, the power supply for iontophoresis is only caused by the electromotive force E of the biocell.

The CPU 6 has a separate driving power supply for driving the CPU itself in inside thereof as shown in FIG. 2B. Alternatively, an external power supply for CPU may be used as shown in FIG. 2C. In other embodiments, the power supply to be used for CPU may be of either an internal type or an external type.

In the transdermal administrating device mentioned above, it is not necessary to provide another power supply for applying bias, which results in further miniaturization of the devices.

Moreover, it may be considered that even when the bottom surface of the conductive electrode layer and the surface of the inert electrode 4 are coated with the same electro conductive materials, the electromotive force E generating between the active electrode 2 and the inert electrode 4 does not vary.

Therefore, even when the active electrode 2 and the inert electrode 4 are coated with other electro conductive materials, they can apply as transdermal administrating devices. For example, if the surfaces of electrodes are coated with electro conductive carbon having a lower chemical reactivity, a denaturation of the surface compositions of electrodes may preferably be avoided at the contact surface of the drug and the skin.

The transdermal administrating device of the present invention is described in detail under with reference to drawings.

FIG. 3 shows the arrangement representing the transdermal administrating device X according to Example 1 of the present invention.

Figure 3A:
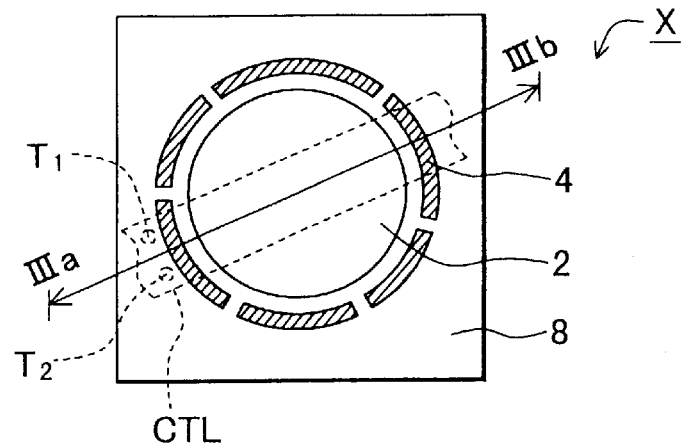
FIGS. 3A, 3B and 3C show an arrangement of the transdermal administrating device used in Example 1 according to the present invention.
Figure 3B:
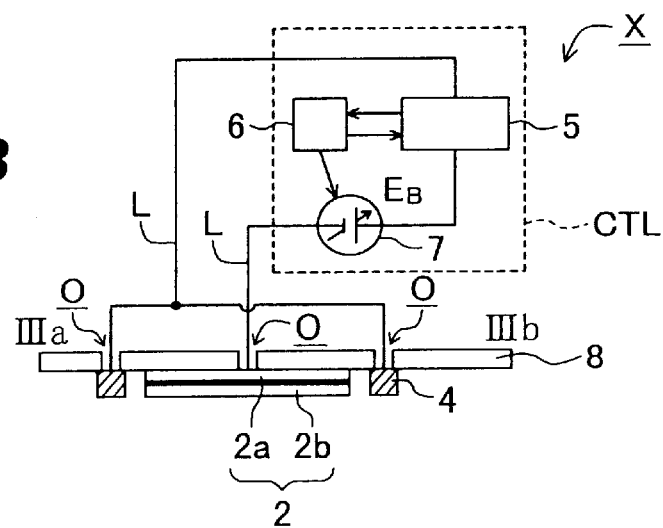

FIG. 3A is a plane view of the transdermal administrating device at the dermocontact side. FIG. 3B is a cross-sectional view of the device taken along the IIIa–IIIb line in FIG. 3A and a schematic view of other components (interconnections) of the transdermal administrating device X.

As shown in FIG. 3A and FIG. 3B, the transdermal administrating device X comprises an active electrode 2 having a conductive electrode layer 2a and a conductive drug layer 2b coated over the whole bottom surface of the conductive electrode layer and an inert electrode 4 formed in the vicinity of the active electrode 2.

Moreover, a sticking plaster (a dermocontact means) 8 is applied on the back side of the conductive electrode layer 2a and that of the inert electrode 4 of the active electrode 2 to cover them.

As shown in FIG. 3B, a control circuit CTL comprises an external load 5, CPU 6, and the bias DC power supply 7. The output voltage of the bias DC power supply 7 is designated as $E_B$. The output voltage of the bias DC power supply 7 is variable.

The control circuit CTL is electrically connected to the active electrode 2 and the inert electrode 4 through the sticking plaster 8. The control circuit CTL may be attached to the dermocontact means 8, for example, removably with connection terminals T1, T2 such as snaps or hooks.

Figure 3C:
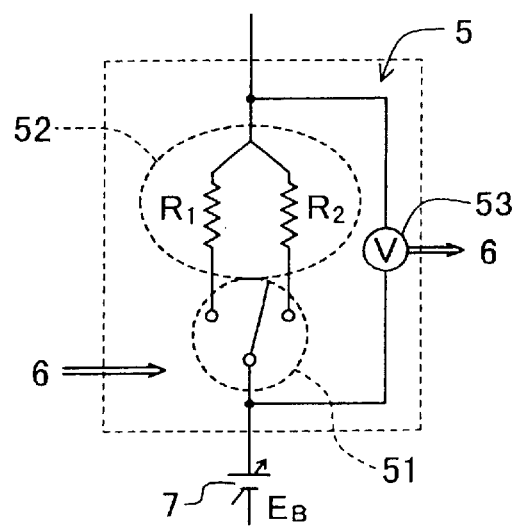

In the device shown in FIGS. 3A to 3C, the active electrode and the inert electrode act also as electrodes for detecting internal resistances (a set of the first and the second the conductive electrode layer).

The conductive electrode 2a constituting a part of the active electrode 2 is made of an iron film having a thickness of 35 μm coated with gold of 3 μm in thickness. The active electrode 2 has a circular configuration of 20 mm in diameter.

The inert electrode 4 is made of a 35 μm-thick iron film whose surface is coated with an oxygen-deficient type zinc oxide (n-type semiconductor). The oxygen-deficient type zinc oxide was produced by plating the surface of the iron film with zinc to a thickness of 5 μm and then oxidizing the surface of the zinc.

In more detail, the Zn surface layer becomes ZnO:Zn (excess zinc type zinc oxide). The proportion of oxygen is reduced from the surface to the interior. The oxygen-deficient type (zinc excess type) zinc oxide is represented by the chemical formula $ZnO_{1-x}$. The x increases toward the interior. The higher the x, the color approaches black.

The inert electrode 4 is, for example, in the form of a roughly belt ring concentric with the active electrode 2. The inert electrode 4 has a width of, for example, about 2 mm. In fact, the inert electrode 4 is separated into six sectors along the periphery by six gaps. This may be capable of preventing current concentration and effective to achieve a wide conductive area. The active electrode 2 and the inert electrode 4 are placed, for example, 3 mm apart from each other.

The semiconductor side of the inert electrode 4 may be directly contacted with skin, but it may be placed in contact with skin after an electro conductive gel is coated on the surface to improve the conductivity.

The conductive drug layer 2b is applied on the bottom surface, preferably the whole bottom surface of the conductive electrode layer 2a. The conductive drug layer 2b has a thickness of, for example, about 0.5 mm. The conductive drug layer 2b may comprise, for example, an aqueous plastic gel containing 0.1 mol % $Na_3N$ dispersed with 2 mol % L-ascorbil magnesium phosphate.

The active electrode 2 having the conductive drug layer 2b and the inert electrode 4 having no conductive drug layer are attached to and fixed on a stick side of a dermocontact means 8 such as sticking plaster.

The dermocontact means 8 is provided with a plurality of openings O (through-hole). The openings O allow a part of the surface of each piece of the inert electrode 4 and a part of the surface of the active electrode 2 to be exposed.

Lead L is taken out through each opening O of the inert electrode 4. The leads L taken out from each opening O are connected to a main lead. The main lead connects the six sectors of the inert electrode 4. Between the main lead and the lead from the active electrode 2, there are connected the external load 5 and the bias DC power supply 7 in series as shown in FIG. 3B.

As shown in FIG. 3C, the external load 5 contains an electronic switch 51 for switching, a standard resistor $R_i$ (i=1,2) 52 and a DC potentiometer 53.

The negative terminal and the positive terminal of bias DC power supply 7 are connected to the active electrode 2 and the inert electrode 4, respectively.

The CPU 6 contains a power supply for self-driving. The CPU 6 has storage function, indicating function, arithmetic function and the like. It may have a displaying function for displaying arithmetic results on a display device.

In this Example, the conductive electrode layer 2a of the active electrode 2 and the inert electrode 4 are made of materials having different standard single electrode potentials and have an arrangement acting also as a set of the first and the second sensor electrodes for $R_d$ detection.

When the concentration of drug ions in the subcutaneous tissue is measured, the CPU 6 instructs the electronic switch 51 to select the resistor $R_i$. The electronic switch 51 operates to switch the resistor $R_1$ and the resistor $R_2$ in a short time (about 0.01 second). A voltage drop between both terminals of each of the resistor $R_1$ and $R_2$, i.e., $V_1$ and $V_2$ are read and the $R_d$ is obtained by calculation according to the equation (1). When the concentration of drug ions is not to be measured, a resistor $R_1$ is inserted in the circuit.

A predetermined resistor value $R_{d0}$ desired to be preserved corresponding to a target concentration of drug ions in the subcutaneous tissue (an appropriate concentration) is stored in the CPU 6. When the actual value of $R_d$ obtained by measurement and calculation is higher than the predetermined value $R_{d0}$, the CPU 6 instructs the bias DC power supply 7 to increase $E_B$. When the value of $R_d$ obtained by measurement and calculation is lower than the value $R_{d0}$, the CPU 6 instructs the bias DC power supply 7 to decrease $E_B$.

After the commencement of flowing a current, the $R_d$ calculated during the transient condition as the drug(s) being permeating into the subcutaneous tissue is fed back to the bias voltage, which helps to reduce the period of transient time. In order to obtain a $R_{d0}$ corresponding to the appropriate concentration of drug ions in the subcutaneous tissue to be stored in the CPU 6, it is preferable to previously prepare a calibration line representing the relationship between the concentration of drug ions in the subcutaneous tissue $[M^-]_1$ and the $R_d$ by conducting experiments.

Transdermal administrating devices were attached on the back of each body of HWY hairless rats. A number of the rats were three a group. The concentration of L-ascorbic acid in blood was chemically detected to control the drug concentration in the blood $[M^-]$. The procedure thereof is described hereunder.

First, a calibration line was prepared. The $E_B$ was set at 1.5 V and the transdermal administrating device was attached on the back of each of the test rats.

The $R_d$ was determined at 30 minutes, 1, 2, 3, 4 and 5 hours after the beginning of flowing a current. In addition, blood examination for the rats was performed at those times. From the blood examination, the concentration of ascorbic acid in blood $[M^-]$ was determined.

Figure 4:
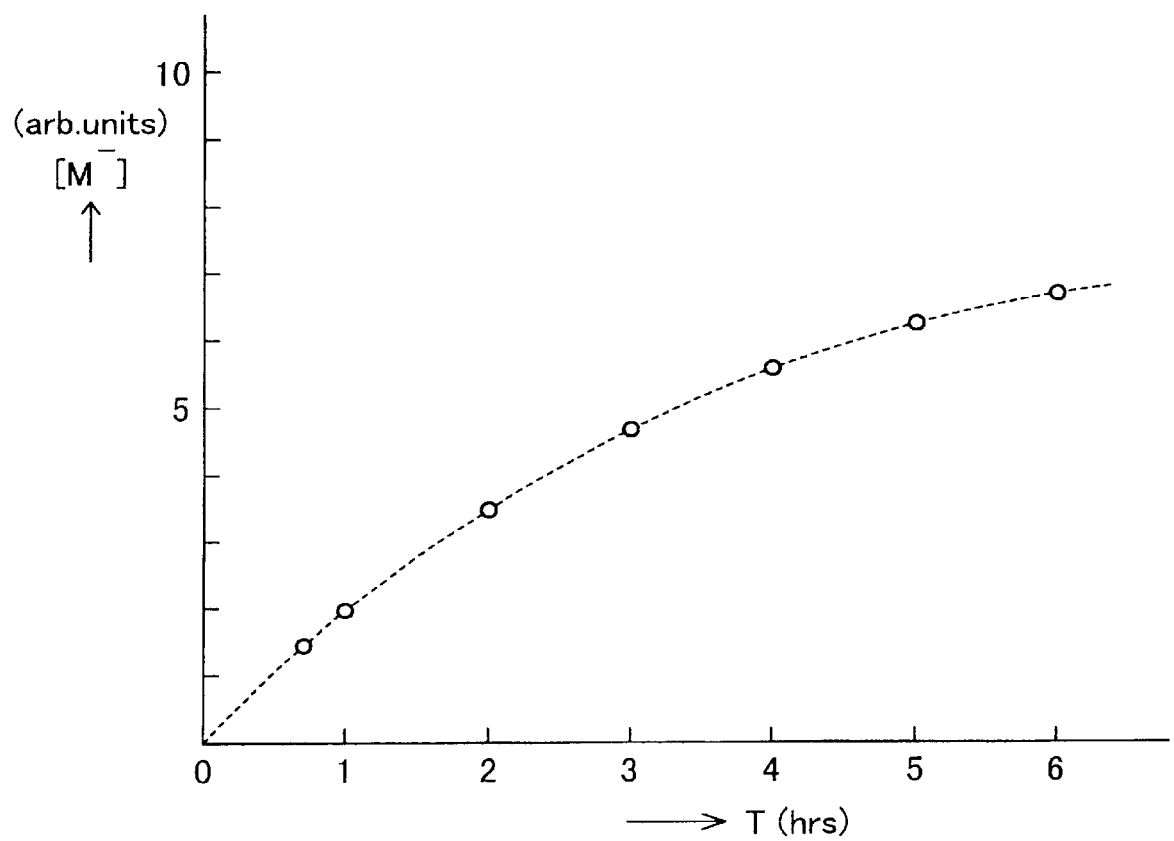
FIG. 4 is a graph representing a relationship between the concentration of L-ascorbic acid in blood and the time (T) elapsed after the beginning of flowing a current, which was obtained from the non-controlled experiment in concentration using with the transdermal administrating device in Example 1 according to the present invention.

FIG. 4 shows the relationship between the concentration of ascorbic acid in blood $[M^-]$ and the elapsed time T after the beginning of flowing a current. As the time T is increased, the concentration of ascorbic acid in blood $[M^-]$ increases almost monotonically. A calibration line was prepared based on the relationship between the obtained $[M^-]$ data and the $R_d$.

Figure 5:
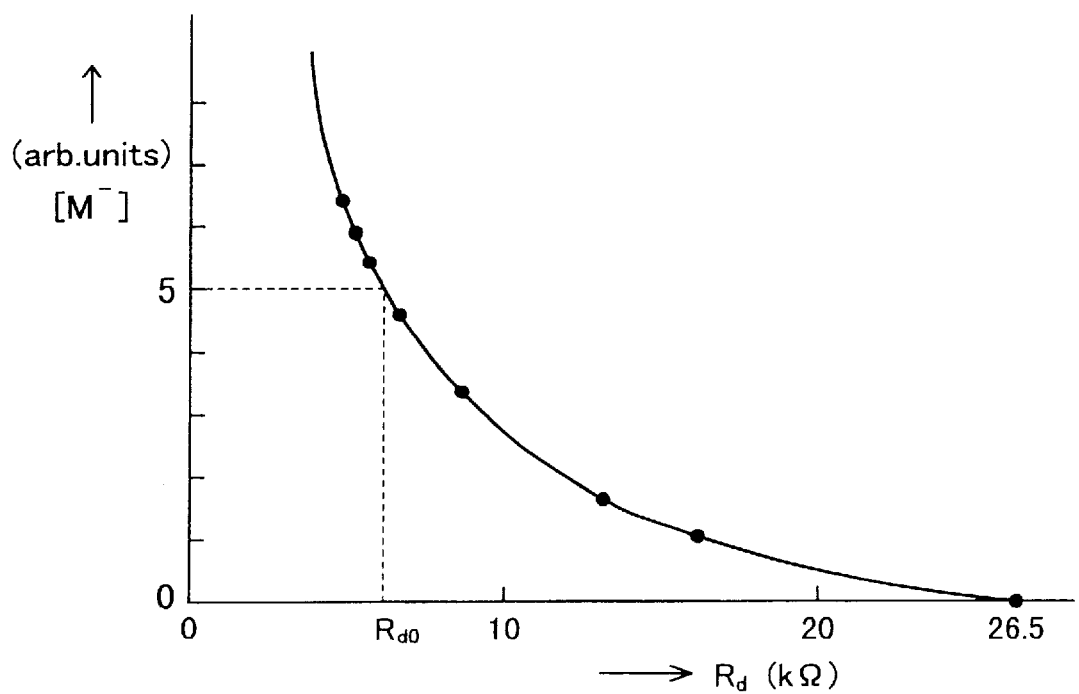
FIG. 5 is a calibration line representing a relationship between the internal resistance of the subcutaneous tissue and the concentration of L-ascorbic acid in blood when the transdermal administrating device in Example 1 according to the present invention was used, which was obtained based on the graph of FIG. 4.

FIG. 5 shows the calibration line representing the relationship between the $R_d$ and the concentration of ascorbic acid in blood $[M^-]$. With an increase in the $R_d$, the concentration of ascorbic acid in blood $[M^-]$ decreases rapidly.

The respective values included in the calibration line have a individual difference. Therefore, one calibration line should preferably be prepared individually.

Next, using the calibration line shown in FIG. 5, the concentration of ascorbic acid in blood [M⁻] was promptly converged to a constant value.

According to the indication from the CPU 6, the bias DC power supply 7 was operated to set $E_B$=8V.

When the concentration of ascorbic acid in blood [M⁻] should be maintained at a constant value, for example, at 5 (arb. unit) in FIG. 5, the $R_{d0}$ should be 6.3 kΩ (kilo ohm) based on the calibration line shown in FIG. 5.

In fact, the measurement and calculation of the $R_d$ was performed according to the indication from the CPU 6 at the time of 10 minutes, 20 minutes, 30 minutes, 40 minutes, 50 minutes, 1 hour, 2 hours, 3 hours, 4 hours, and 5 hours elapsed after the beginning of flowing a current. In this case, when the $R_d$ was determined, the $E_B$ was temporarily changed to 1.5 V and the voltage drop $V_i$ at the external load was measured.

At the measurement after the current flowing time has elapsed for 20 minutes, the $R_d$ was lower than the $R_{d0}$. The CPU 6 operated to feed back the bias voltage to reduce the bias voltage $E_B$.

Figure 6:
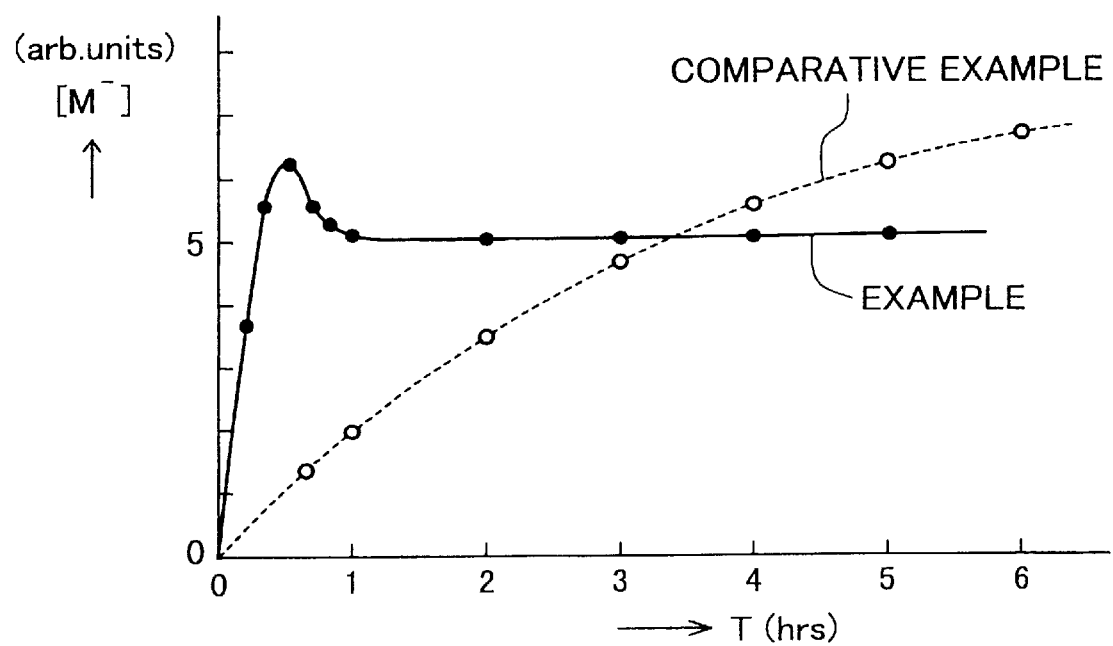
FIG. 6 shows a graph (solid line) representing a relationship between the controlled concentration of L-ascorbic acid in blood and the time (T) elapsed after the beginning of flowing a current when the transdermal administrating device in Example 1 according to the present invention was used with operating the feedback system and a graph (dotted line) representing a comparative example without the feedback mechanism.

More particularly, the voltage was temporarily reduced to 0.5 V and finally increased to about 1.1 V A variation in the concentration of ascorbic acid in blood [M⁻] with time and the aforementioned values in FIG. 4 are shown in FIG. 6 with a solid line and with a dotted line, respectively. The [M⁻] calculated from the $R_d$ overshot to the value of about 6.5 within one hour after the beginning of flowing a current and then converged to almost a constant value of 5 about 1.5 hours after the beginning of flowing a current. Comparative Example indicates that with $E_B$=1.5 V, blood drug concentration [M⁻] was still increasing not converging to a constant value even at 5 hours after the beginning of flowing a current.

From the results as described above, it can be understood that the transdermal administrating device according to the present invention is useful to control the concentration of ascorbic acid in blood.

The n-type semiconductor ZnO, the material constituting the inert electrode 4 used in this Example forms a Schoftky barrier at the dermocontact interface preventing OH⁻ ions to penetrate into the inside of ZnO so as to form an insulating material, zinc hydroxide, which has an effect of generating stably the electromotive force.

The generation of overshooting in FIG. 6 is considered owing to the unchanged bias until the $R_d$ became lower than $R_{d0}$. Measuring variation in $R_d$ and commencing prospect control will be able to reduce the amount of overshooting. For this purpose, a register storing past data of $R_d$ should be provided in the CPU 6.

Figure 7A:
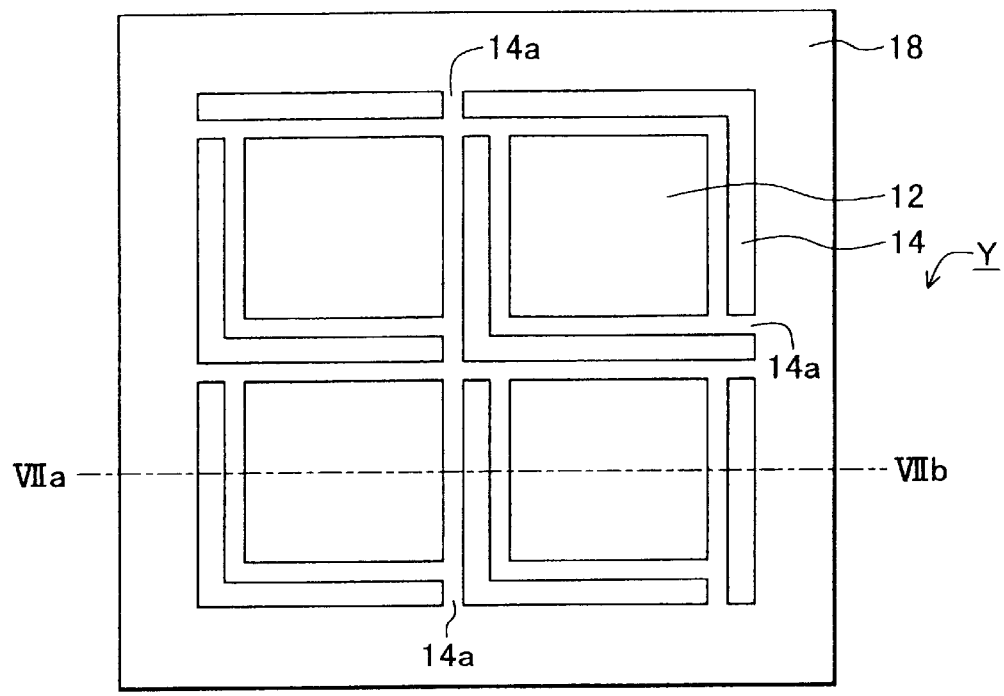
FIGS. 7A and 7B show an arrangement of the transdermal administrating device used in Example 2 according to the present invention.
Figure 7B:
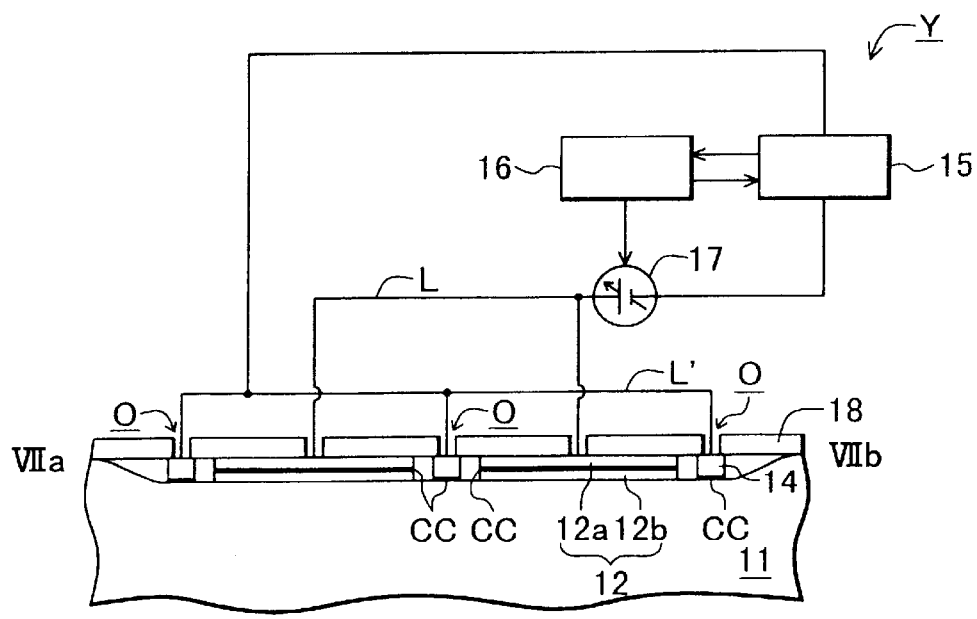

FIGS. 7A and 7B show the transdermal administrating device according to Example 2 of the present invention. FIG. 7A is a plane view of the dermocontact side of the transdermal administrating device. FIG. 7B is a cross-sectional view of the device taken along the line VIIa–VIIb and a schematic view of the components of the device in the non-dermocontact side. Again, in this Example, the conductive electrode layer 12a of the active electrode and the inert electrode 14 act also as a set of the first and the second sensor electrodes [electrodes for detecting internal resistance (a set of the first and the second conductive electrode layers)].

Referring to the transdermal administrating device Y, the conductive electrode layer 12a constituting the active electrode 12 has a lower electron affinity than that of the inert electrode 14. The drug layer-contacting side of the conductive electrode layer 12a and the dermocontact side of the inert electrode 14 are coated with a film of the same material.

The conductive electrode layer 12a comprises an iron film of a thickness of 30 μm whose whole surfaces are first coated with an evaporated Mg—Zn film of a thickness of 0.5 μm and then the dermocontact surface is further coated with an evaporated conductive carbon film CC of a thickness of 3 μm on the Mg—Zn film.

The inert electrode 14 comprises an iron film of a thickness of 30 μm whose whole surfaces are coated with an evaporated Pd film of a thickness of 3 μm and then one surface is coated with an evaporated conductive carbon film CC of a thickness of 3 μm on the Pd film. On the conductive carbon film CC of the conductive electrodes layer 12a, a conductive drug layer 12b of a thickness of about 1 mm is coated. The conductive drug layer 12b is composed of a conductive plastic gel containing 1 mol % Valethamate bromide and 0.1 mol % NaBr dispersed.

The dense carbon film CC is chemically stable. Particularly the material constituting the conductive electrode layer 12a, i.e., the Mg—Zn alloy is protected from oxidation with moisture and chemical agents. Therefore, a stable electromotive force can be produced over an extended period of time.

As is shown in FIG. 7A, the active electrode 12 having the conductive electrode layer 12a, whose bottom surface is coated with the conductive drug layer 12b, has roughly a square configuration as a whole, but in fact it is separated into four square sections.

The inert electrode 14 is disposed so that two regions surround each section of the active electrode 12. The inert electrode 14 and the active electrode 12 are spaced 2 mm from each other. The inert electrode 14 has a plurality of gaps 14a and has a shape like a strip of 2 mm in width. Anti-skin surface of the active electrode 12 and the inert electrode 14 are attached to a dermocontact means 18 such as a sticking plaster. The dermocontact means 18 has a plurality of openings O formed for exposing the surfaces of the active electrode 12 or the inert electrode 14. Each section of the active electrode 12 and the inert electrode 14 has at least one opening formed.

As is shown in FIG. 7B, sections of the divided active electrode 12 disposed are connected one another with leads L. The leads L each connected to an active electrode section are collected on the non-dermocontact side of the dermocontact means 18 into one lead which is connected to the positive terminal of the DC power supply 17 for applying a bias voltage.

The leads L' each connected to the non-dermocontact side of each inert electrode section are collected on the non-dermocontact side of the dermocontact means 18 into one lead which is connected to the negative terminal of the bias DC power supply 17 via the external load. The internal structure of the external load 15 is similar to that shown in FIG. 1B. Moreover, a CPU 16 is provided between the external load 15 and the bias DC power supply 17 in order to receive a signal from the external load 15, effect arithmetic operation, store, and give an instruction to be fed back to the bias voltage $E_B$ of the bias DC power supply 17.

Since the effective component of the conductive drug layer 12b is cationic, the bias DC power supply 17 is connected in such a manner as its positive terminal is connected to the active electrode 12.

When the transdermal administrating device Y of Example 2 is placed in contact with skin by the dermocontact means 18, a chemical cell with the inert electrode 14 as a positive electrode and the active electrode 12 as negative electrode is formed even when $E_B$=0.

A direct current flows through a closed circuit containing the conductive drug layer 12b and the skin tissue 11. This electromotive force is attributed to both the power supply 17 and a difference in standard single electrode potential between the positive electrode, Pd, and the negative electrode, Mg—Zn alloy. The carbon film CC formed on one side of the active electrode 12 and that formed on one side of the inert electrode 14 have the same components.

Therefore, the influence of the carbon film CC on the standard single electrode potentials (i.e. electron affinity) of the active electrode 12 and the inert electrode 14 can be offset to cause no effect on the electromotive force.

When the materials coated on one side of the active electrode 12 and that of the inert electrode 14 are different from each other, they will have an effect on the electromotive force of the chemical cell. If this effect is taken into account, this arrangement may be employed.

The transdermal administrating device Y as shown in FIGS. 7A and 7B was produced. A dimension of the device excluding the dermocontact means 18 was 25×25 mm$^2$. This device was attached on the back of a nude mouse to measure a variation in the concentration of Valethamate in blood [M$^+$] with time. One group was consisted of three mice.

A calculation line was prepared as in previous Example by setting $E_B$=3V and measuring the $R_d$ at predetermined times after the beginning of flowing a current and effecting the arithmetic operation. The concentration of Valethamate in blood [M$^+$] was also obtained by blood examination.

Figure 8:
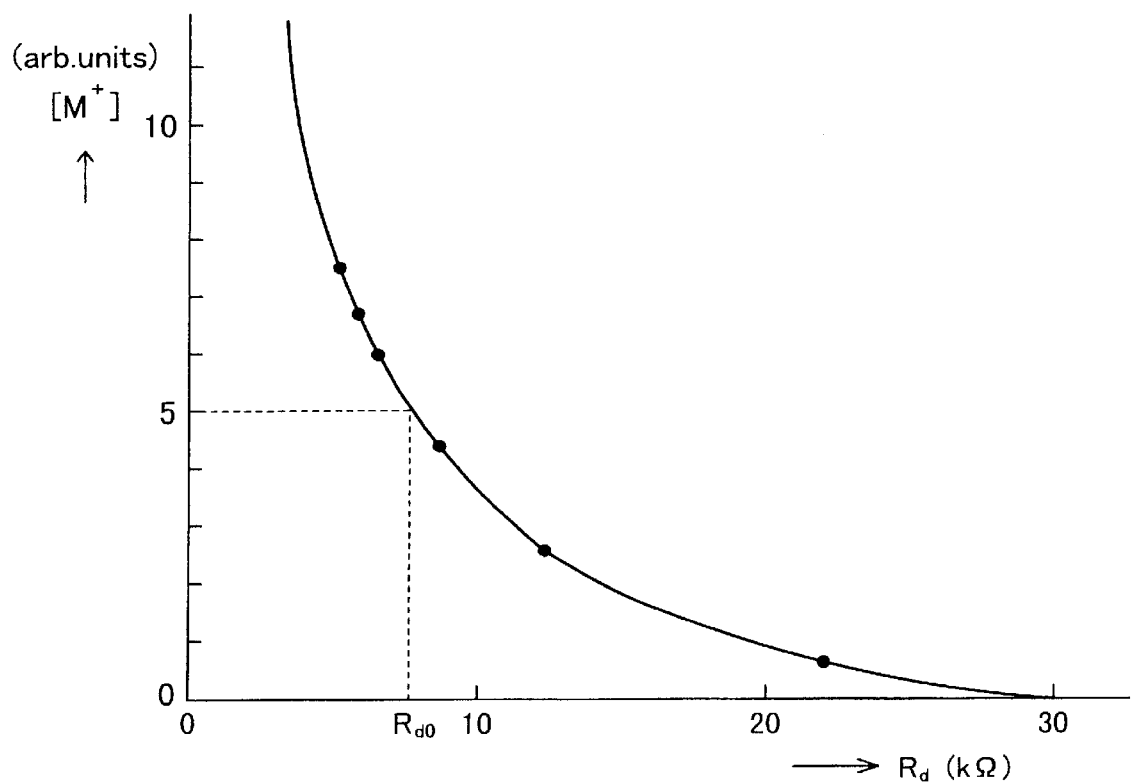
FIG. 8 is a calibration line representing a relationship between the internal resistance of the subcutaneous tissue and the concentration of Valetamate in blood when the transdermal administrating device in Example 2 according to the present invention was used.

FIG. 8 shows the calibration line representing the relationship between the concentrations of Valethamate in blood [M$^+$] and the $R_d$, obtained by using the transdermal administrating device Y of Example 2. As the $R_d$ increases, the concentration of Valethamate in blood [M$^+$] is rapidly decreased. It can be seen that when the concentration of Valethamate in blood [M$^+$] is to be kept at 5 (arb unit), the $R_d$ should be at 7.5 kΩ (kilo ohm). The $R_d$ before administration was about 32 kΩ (kilo ohm).

Next, with setting the concentration of Valethamate in blood to be controlled at 5 (arb. unit), experiments of controlling the concentration were performed.

Figure 9:
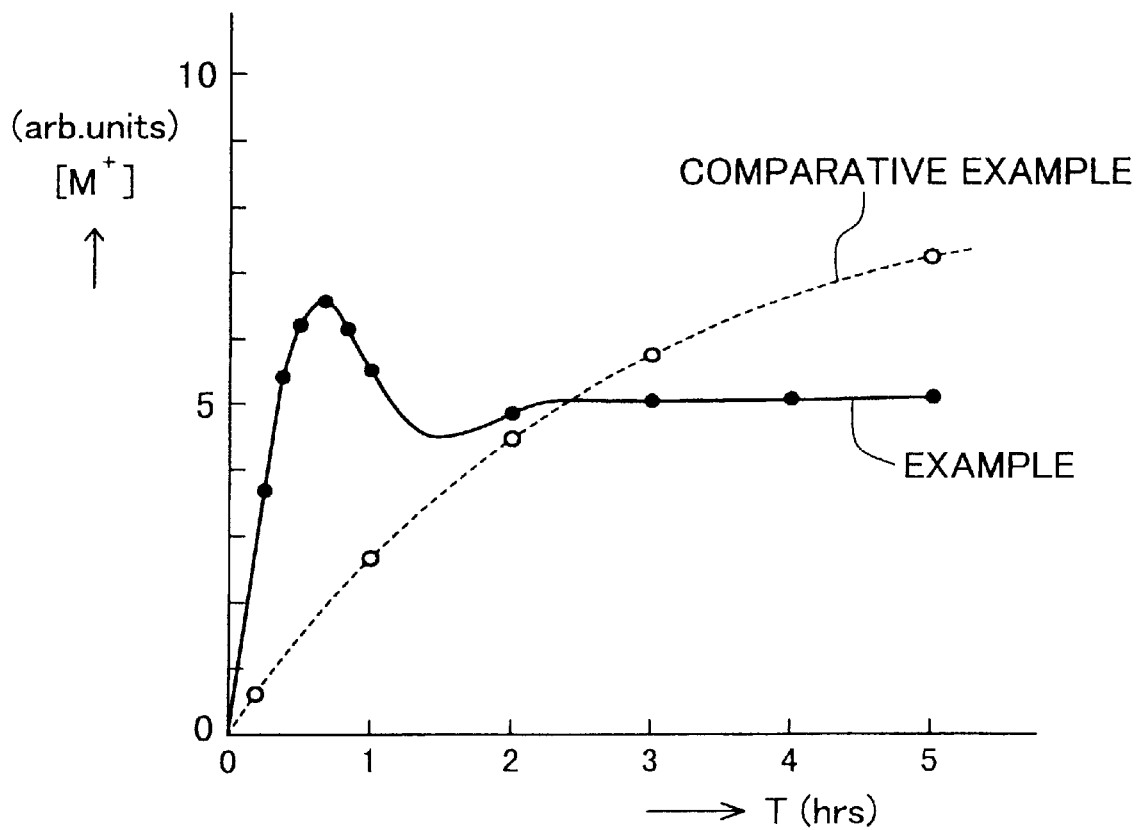
FIG. 9 shows a graph (solid line) representing a relationship between the concentration of Valetamate in blood and the time (T) elapsed after the beginning of flowing a current when the transdermal administrating device in Example 2 according to the present invention was used to administrate the Valetamate and a graph (dotted line) representing a comparative example without the feedback mechanism.

FIG. 9 shows the variation in the concentration of Valethamate in the blood [M$^+$] with time when $R_{d0}$ was 7.5 kΩ (kilo ohm) as a solid line. $E_B$ was initially set at 7 V, and the $R_{d0}$ was input into the CPU 6 as a target level for feedback control. The transdermal administrating device Y was placed in contact with the skin and the current was initiated to flow. The CPU 16 (FIG. 7B) measured the $R_d$ at 10 minutes, 20 minutes, 30 minutes, 40 minutes, 50 minutes, 1 hour, 2 hours, 3 hours, 4 hours, and 5 hours after the beginning of flowing a current and effected the arithmetic operation.

When the $R_d$ is measured, $E_B$ was temporarily set at 3V. As a result of the $R_d$ control performed by the CPU 6, the concentration of Valethamate in blood [M$^+$] increased up to about 6.5, and then undershot to 5 or less once. The concentration of Valethamate in blood [M$^+$] converged to the predetermined concentration of 5 (arb. unit) at about 2 hours after the beginning of flowing a current.

In the above two Examples, the power supplies provided in the transdermal administrating devices were of DC.

In case the voltage applied to the skin is lower, the use of DC bias does not cause any problem. If a high voltage is applied to the skin, the risk of damaging the skin becomes higher.

There was observed a case where the nude mice were damaged on their skin at 3 hours or more after the beginning of flowing a current when $E_B$ was set at high level in Example 2.

In this case, application of pulsed current is effective since intervals of flowing no current are given to the skin tissue.

Figure 10A:
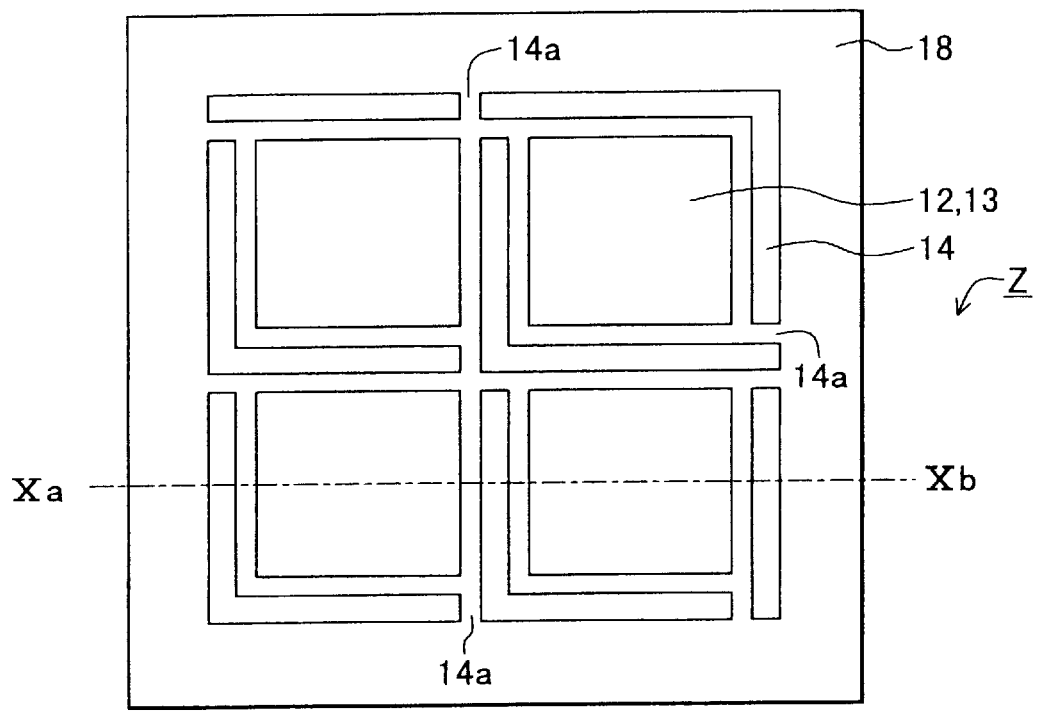
FIGS. 10A and 10B show an arrangement of the transdermal administrating device used in Example 3 according to the present invention.
Figure 10B:
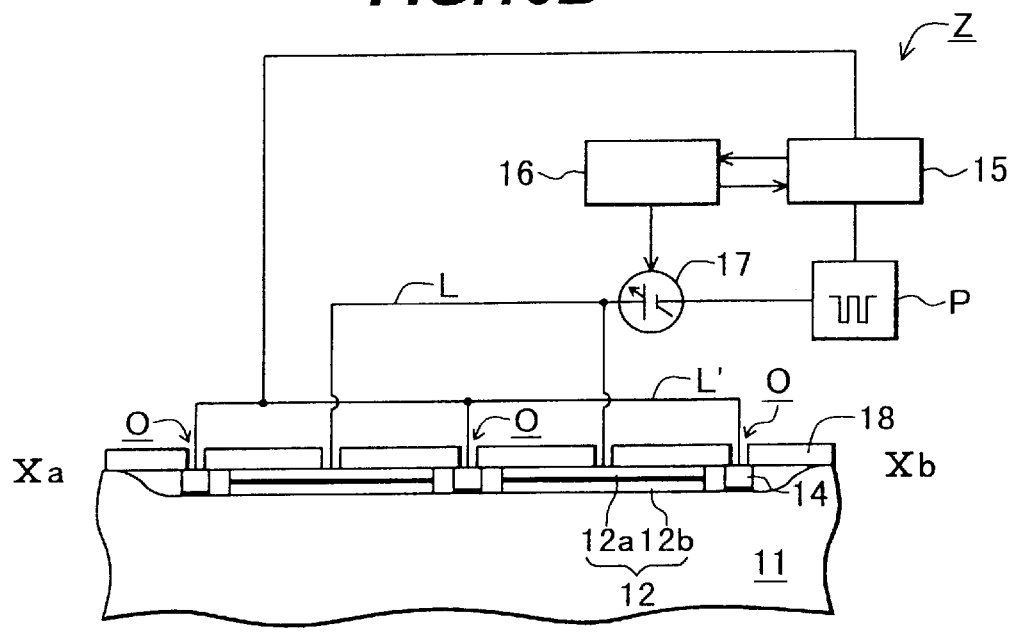

FIGS. 10A and 10B show the transdermal administrating device according to Example 3 of the present invention. FIGS. 10A and 10B are corresponding to FIGS. 7A and 7B, respectively.

The transdermal administrating device Z according to Example 3 was provided with a pulse signal generating circuit P between the bias DC power supply 17 and the external load 15.

This transdermal administrating device was loaded on the back of nude mice to permit the permeation of Valethamate. The duty ratio of the pulse signal was set at ⅓. The $E_B$ was initially set at 10 V.

No damage was observed on the skin of the nude mice even at 10 hours elapsed after the beginning of flowing a current.

In the above Examples 1 to 3, the set of the electrodes for iontophoresis (the active electrode and the inert electrode) acts also as sensor terminals for detecting an subcutaneous tissue resistance during flowing a current therethrough, i.e., electrodes for a chemical cell (electromotive force E) with the skin tissue and the drug layer as electrolytes.

As the bias DC voltage $E_B$ becomes higher, the $R_d$ given by the equation (2) becomes lower and the sensitivity of detecting the concentration of drug in the subcutaneous tissue is reduced. In addition, when the $R_d$ is detected, $E_B$ must be reset at the value used at the calibration-line preparation. Moreover, when a pulsed current is used, the $R_d$ must be measured in a condition of the pulsed current being temporarily stopped. These difficulties occur in this case. To cope with the difficulties, sensor terminals for detecting the $R_d$ may be provided in the drug permeation area besides the active electrode and the inert electrode.

Figure 11A:
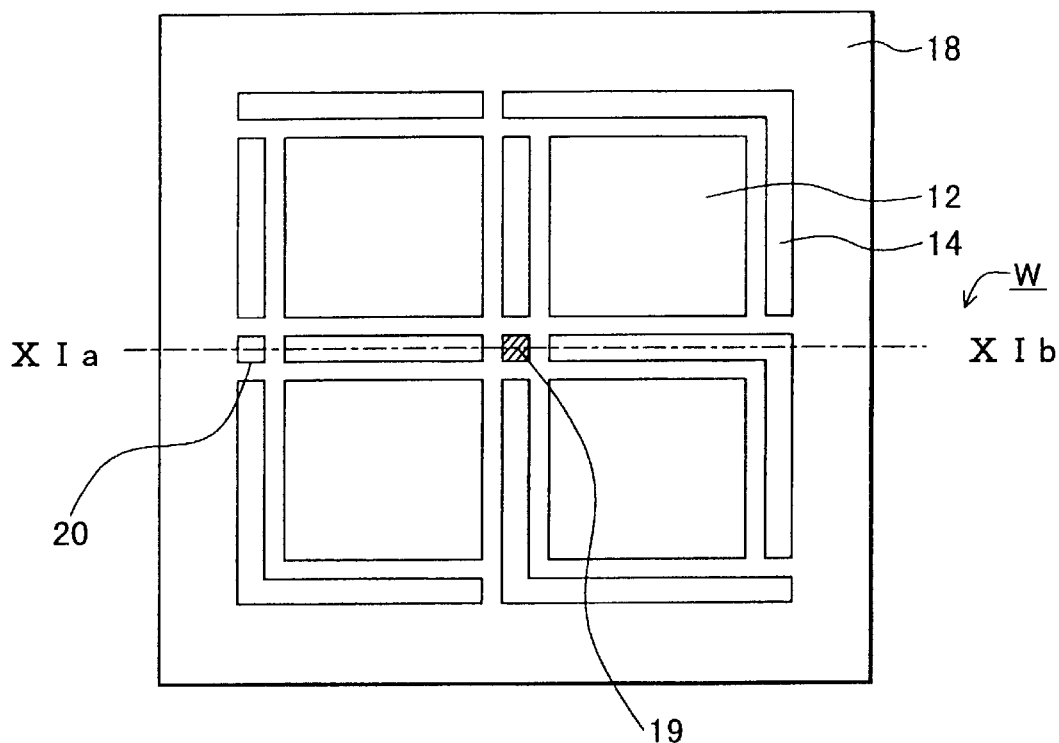
FIGS. 11A and 11B shows an arrangement of the transdermal administrating device used in Example 4 according to the present invention.
Figure 11B:
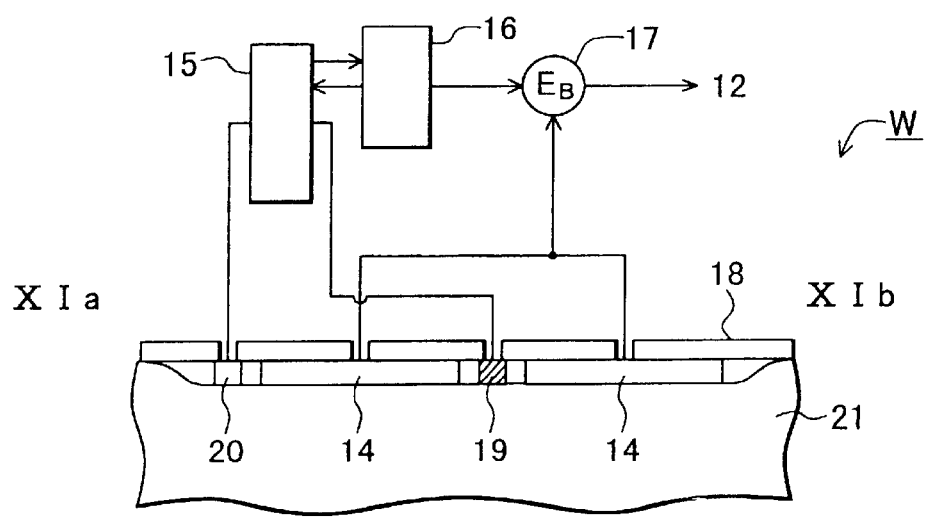

FIGS. 11A and 11B show the arrangement of the transdermal administrating device according to Example 4 of the present invention.

The transdermal administrating device W as show in FIGS. 11A and 11B has the first electrode 19 and the second electrode 20 for detecting the $R_d$ provided as a set of the first and second sensor electrodes, which is different from the transdermal administrating device as shown in FIG. 7. FIG. 11A shows a top plane view of the dermocontact side of the transdermal administrating device W, and FIG. 11B shows a cross-sectional view of the device taken along the line XIa–XIb in FIG. 11A. FIG. 11B shows also a part of interconnections on the anti-skin side of the transdermal administrating device W. A chemical cell is formed between the positive electrode 19 and the negative electrode 20. The positive electrode 19 and the negative electrode 20 are disposed in the vicinity of the area where drug ions are permeated. Each of the electrodes 19 and 20 may have any optional configuration and a small area because it is provided only for detecting the $R_d$. The standard single electrode potential (electron affinity) of the material constituting the positive electrode 19 is higher than that of the negative electrode 20. The material constituting the electrodes 19 or 20 may be either the same as or different from those constituting the conductive electrode layer 12a contained in the active electrode 12.

The each inert electrode 14 is connected to one lead and each lead is collected on the back side of the dermocontact means 18 into one lead which is connected to one of the terminals of the bias DC power supply 17.

The other terminal of the bias DC power supply 17 is connected to the lead from the active electrode. A set of the $R_d$ detecting electrode 19 and 20 is connected to the external load 15 on the backside of the dermocontact means 18 to form a closed circuit. The external load 15 to be used may be the same as that used in Examples 1 to 3.

In the transdermal administrating device W according to Example 4, the $R_d$ detecting circuit is substantially separated from the bias circuit for the iontophoresis. CUP 6 is connected to the external load 15 of the $R_d$ detecting circuit and the bias circuit 17 for iontophoresis to perform instructions such as indication, measurement, arithmetic operation, storage, feedback and the like. It is possible to control stably and easily the concentration of drug(s) in the subcutaneous tissue.

Moreover, a pulse generating circuit for pulsing the current for the iontophoresis may be added in the bias circuit.

When the $R_d$ detecting terminals and the electrodes for the iontophoresis are arranged to be substantially separated from each other as in the transdermal administrating device W of Example 4, iontophoresis may be conducted only by the DC power supply 17.

Therefore, materials to be used for constituting the conductive electrode layer 12*a* and the inert electrode 14 may be chemically stable and cheap material having the same standard single electrode potential. Moreover, it is possible that either the active electrode 12 or the inert electrode 14 may be utilized as a sensor terminal for detecting the $R_d$ to form a detecting circuit with the detecting electrode 19 or the detecting electrode 20.

In a case where the detecting terminals are completely separated from the electrodes for the iontophoresis as in the transdermal administrating device W shown in FIGS. 11A and 11B, the equation (2) is used for controlling the drug concentration in blood. If the conductive electrode layer 12*a* and the inert electrode 14 are constituted with the same material, the bias circuits for iontophoresis becomes a simple load circuit where the skin leakage resistance ($R_p$+$R_s$) and the resistance $R_d$ to the current flowing through subcutaneous tissue are connected in parallel, allowing it to be easily handled.

However, it is necessary to control taking into account that the iontophoresis circuit and the $R_d$ detecting circuit are different in the space between electrodes and in the electrode surface areas, and therefore, that the value of $R_d$ is different between both the circuits.

The dimensions and the components of the transdermal administrating device W according to Example 4 as shows in FIGS. 11A and 11B may be identical to those of the transdermal administrating device shown in FIGS. 7A and 7B. By performing the iontophoresis with nude mice, the concentration of Valethamate in the blood can be controlled similarly to the case in Example 3 as shown in FIGS. 10A and 10B. Thus, the $R_d$ detection and the control of the $E_B$, hence of the [M$^-$] can be affected by using another terminals to achieve the continuous control of $E_B$. The flowing current also can easily be pulsed.

In the mass production of the transdermal administrating devices according to Examples 1 to 4, the dermocontact means 18 and the components arranged on the dermocontact side by said means may preferably be disposed after use. The electric circuit section located on the backside of the dermocontact means 8 also may preferably be made reusable.

In Examples as shown in FIGS. 3A to 11B, the rate of permeation of effective drug components through the skin was controlled by controlling the voltage $E_B$ of the bias DC power supply. However, as shown in FIGS. 2A to 2C, cases where no bias DC power supply is added to the circuit are included within the scope of the present invention and they can be put into practice.

Figure 12A:
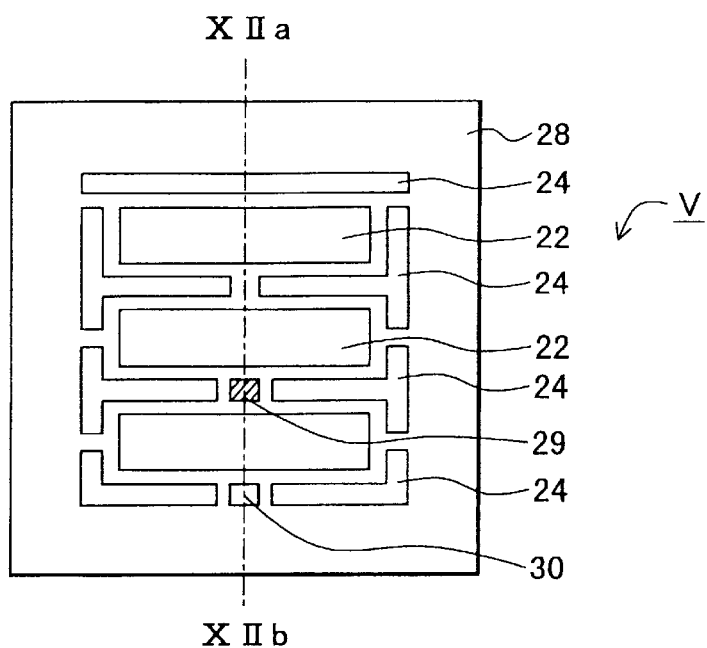
FIGS. 12A and 12B shows an arrangement of the transdermal administrating device used in Example 5 according to the present invention.
Figure 12B:
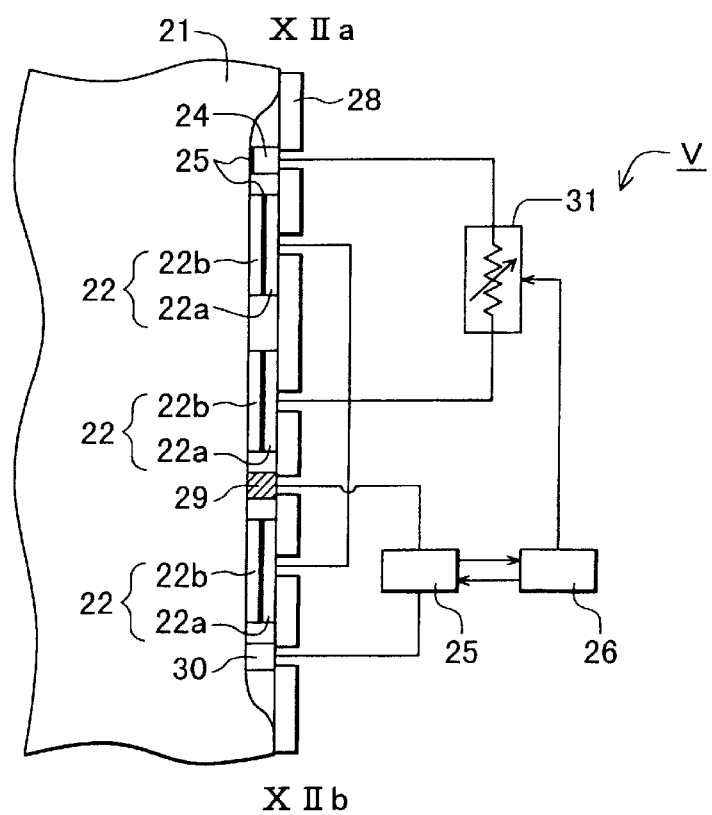

FIGS. 12A and 12B show the transdermal administrating device according to Example 5 of the present invention.

FIG. 12A shows a top plane view of the dermocontact side and FIG. 12B shows a cross-sectional view of the device taken along the line XIIa–XIIb in FIG. 12A and the circuit components on the backside of the dermocontact means 28.

In the transdermal administrating device V of Example 5 as shown in FIGS. 12A and 12B, no bias DC power supply is used.

The conductive electrode layer 22*a* is formed as follows; first, whole surfaces of an iron film of a thickness of 30 μm were sputtered with a $Al_{0.1}Zn_{0.4}Mg_{0.5}$ alloy in a vacuum apparatus and then, spattered onto one side of the alloy film with conductive carbon 25 in the same vacuum apparatus (without breaking the vacuum) and further, sputtered with Zn onto the other side of the alloy film.

A conductive drug layer 22*b* is provided on the conductive carbon 25 formed on the conductive drug layer 22*a*. The conductive electrode layer 22*b* is formed by applying a gel dispersion comprising 1 mol % $K_5[SiVW_{11}O_{40}]$ dispersed in a conductive keratin cream containing 0.1 mol % $K_3N$ to a thickness of about 1 mm.

To the sputtered Zn film of the conductive electrode layer 22*a* is connected a Zn lead.

The inert electrode 24 is formed as follows; first, a whole surface of an iron film of a thickness of 30 μm was plated with Au and then, conductive carbon 25 was sputtered onto the plated Au on one side of the film and further, Zn film was sputtered onto the plated Au on the other side thereof.

The electro conductive carbon sputtered surface is the dermocontact surface, and to the surface sputtered with Zn on the backside is connected a Zn lead. The sections of the active electrode 22 are connected to one lead on the backside of the dermocontact means 28 and then to one of the terminals of a variable resistor 31. Similarly those of the inert electrode 24 are connected to one lead on the backside of the dermocontact means 28 and then to the other one of the terminals of the variable resistor 31.

On the other side, a set of sensor terminals 29 and 30 for detecting the $R_d$ are composed of a pellet comprising n-Ge having a carrier concentration of $1 \times 10^{17}$ cm$^{-3}$ and small Au films, respectively. The terminals 29 and 30 for detecting the $R_d$ are connected to leads on the non-dermocontact side, respectively, and to the external load 25 on the backside of the dermocontact means 28. The arrangement of the external load 25 of the transdermal administrating device V is identical to that of the transdermal administrating device in Example 4. CPU 6 is provided between the external load 25 and the variable resistor 31.

When the transdermal administrating device V according to Example 5 was loaded on the back of a nude mouse, the chemical cell formed by the active electrode 22 and the inert electrode 24 generated an electromotive force of about 2.9 V.

With using the external load 25 instead of variable resistor 31, the $R_d$ value of the iontophoresis circuit obtained by effecting measurement and arithmetic operation before administration of drug was about 30.5 kΩ (kilo ohm).

While in the detecting circuit comprising the detecting terminals 29 and 30 and the external load 25, the $R_d$ value obtained by effecting measurement and arithmetic operation before administration of drug was about 158 kΩ (kilo ohm).

The electromotive force E of the chemical cell comprising the $R_d$ detecting terminals 29 and 30 and the skin tissue was about 1.2 V. Though the electromotive force E and the $R_d$ value are different to a great extent, respectively, between the two circuits, by applying the measurement and arithmetic operation to the $R_d$ of the detecting circuit, a calibration line representing the concentration of hetero-poly acid ions in the blood [M⁻] can be prepared to control the drug concentration in blood based the line.

The transdermal administrating device V according to Example 5 uses no bias DC power supply. The current flowing in the iontophoresis circuit can be controlled by varying the value of the variable resistor 31 to control the concentration of drug(s) permeated into the subcutaneous tissue. For example, when the value of the variable resistor 31 is set at 30 kΩ (kilo ohm), the value of flowing current before permeation of drug(s) can be reduced to about ½.

Polyoxomethalate ion $[SiVW_{11}O_{40}]^{-5}$ has a high permeability so that it allows a sufficient effect to achieve iontophoresis even without connecting a bias DC power supply between the active electrode 22 and the inert electrode 24.

Removing the variable resistor 31 out of the circuit, the measurement and arithmetic operation for $R_d$ and the measurement of the blood concentration in blood [M⁻] were performed to prepare a calibration line representing the relationship between the $R_d$ and the [M⁻].

Next, a $R_{d0}$ value corresponding to a target concentration $[M^-]_0$ was determined from the calibration line and the variable resistor 11 was connected to the circuit.

Figure 13:
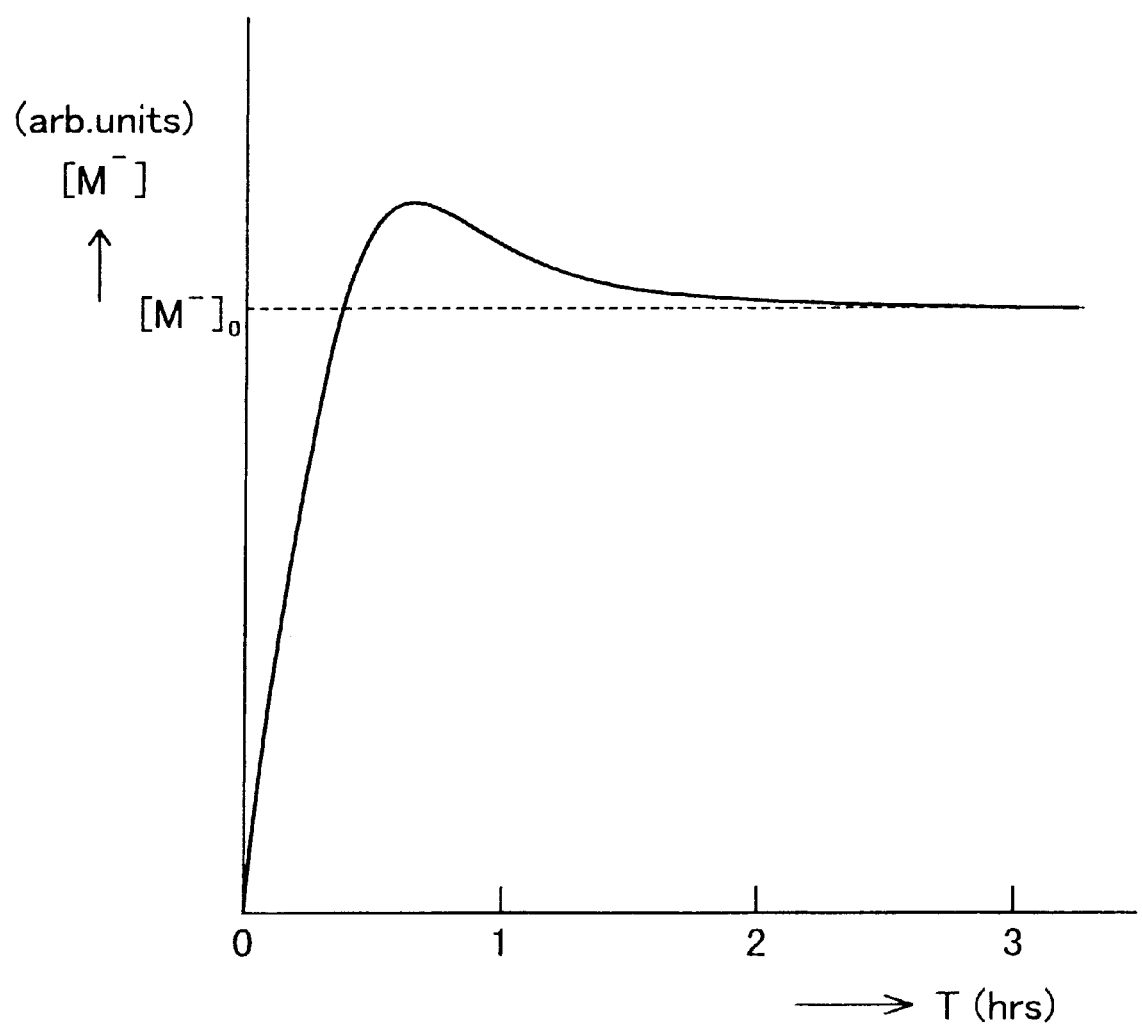
FIG. 13 shows a graph representing a relationship between the concentration of Polyoxomethalate ion in blood and the time (T) elapsed after the beginning of flowing a current when the transdermal administrating device in Example 5 was used.

The concentration of drug was controlled by controlling the value of the variable resistor 31 with measuring the $R_d$ at varying times. As a result, a profile representing a variation in the concentration [M⁻] in blood as shown in FIG. 13 could be obtained.

It can be seen that the concentration in blood [M⁻] is kept at the target concentration after about 2 hours has been elapsed from the beginning of flowing a current.

The transdermal administrating device V according to Example 5 allows the concentration of permeated drug(s) to be controlled by iontophoresis with controlling the current flowing in the circuit, which is different from the case where the bias voltage is controlled.

As has been described in each Example, the active electrode and the inert electrode participating in feeding drugs, and the electrodes participating in the detection of internal resistance (a set of the first and the second conductive electrode layer) may separately provided, or the former may act also as the latter. In case they are separately provided, the standard single electrode potential of the active electrode may be either the same as or different from that of the inert electrode. Alternatively, the active electrode and the inert electrode may act also as either one of the first and the second conductive electrode layer.

As above, the use of the transdermal administrating device according to each Example permits the control of drug concentration in blood, i.e., the data obtained by observing in situ the concentration of drug(s) in the subcutaneous tissue non-invasively are feed to the applied voltage (field strength) or the circuit current (current density) which are the driving force of the permeation of drug ions.

In addition, for various drugs, if a calibration line has been prepared for a specific drug selected with respect to a specific animal species, deviations of correct plots from the calibration line due by varying species may be conveniently compensated by shifting the line to a distance corresponding to the measurement of $R_d$ for each species before the administration of drug.

In the transdermal administrating devices according to embodiments as described above, the components arranged on the dermocontact side of the dermocontact means, i.e., the active electrode containing the conductive electrode layer, and the conductive drug layer, the inert electrode, a set of detecting electrodes, and the dermocontact means can be in principle made disposable. However, a set of detecting electrodes is less deteriorated so that they may be reused. In this case, for example, an arrangement where a set of detecting electrodes and the dermocontact means are made removable from each other will be convenient. Particularly if the connection between both is standardized, it is convenient to attach a new dermocontact means and detecting electrodes.

Moreover, unifying a combination of the active electrode and the inert electrode together with a set of detecting electrodes can make the structure simple. Conversely, if the both are separated, the flexibility about conditions with respect to standard single electrode potentials and sizes is increased though the structure becomes complicated. It will be preferable that the arrangement is varied depending upon the purposes.

The small electronic parts to be provided in the non-dermocontact regions of the dermocontact means can be made to attach with a snap. The transdermal administrating devices can be easily put into work. Therefore, they are excellent in portability and allow the correct administration of drugs to perform without giving patients pain.

As described above, with the transdermal administrating device according to each Example, the blood concentration of the drugs, which are non-invasively permeated by the iontophoresis process, can easily be monitored and its information can be obtained.

The obtained information may be fed back to the conditions for flowing current to control the concentration of drugs at a predetermined value.

As a result, the concentration of a mere trace of drugs in blood can be controlled with the benefits of the locality of transdermal administration and without giving patients pain and without restricting daily activity so that the quality of life of patients can be further improved.

In addition, various drugs can be transdermally administrated.

As above, the present invention has been described with reference to Examples, it is obvious for those skilled in the art that other various alterations, modification, combination and the like can be made.

What is claimed is:

1. A transdermal administrating device comprising:
   an active electrode having a conductive electrode layer and a conductive drug layer applied on one surface of said conductive electrode layer, said conductive drug layer being capable of being placed in contact with skin;
   an inert electrode which is made of a conductive material, and which is capable of being placed in contact with skin and spaced from said active electrode;
   means for applying a variable bias voltage across said active electrode and said inert electrode;
   a set of first and second conductive electrode layers which are each made of a material having a different standard single electrode potential, and which are capable of being placed in contact with skin and spaced from each other;
   a controller connected to said first and said second conductive electrode layers in a non-dermocontact region for measuring an internal resistance of skin tissue between said first and said second electrode layers, said internal resistance being distinct from a contact resistance and a leak resistance between the first and second conductive electrode layers, and controlling an electric current passing through the skin tissue between said active electrode and said inert electrode based on said measured internal resistance; and dermocontact means for keeping said active electrode, said inert electrode, and said set of said first and said second electrodes in contact with skin.

2. The transdermal administrating device according to claim 1, wherein said controller is held by said dermocontact means.

3. The transdermal administrating device according to claim 1, wherein:
said means for applying the variable bias voltage comprises a variable bias power supply connected between said active electrode and said inert electrode in a non-dermocontact region, and
said controller comprises:
a measurement circuit for measuring said internal resistance, and
a controlling circuit for instructing said measurement circuit to measure said internal resistance, calculating a bias voltage to be applied between said active electrode and said inert electrode based on said measured internal resistance value, and instructing said variable bias power supply to apply said calculated bias voltage across said active electrode and said inert electrode.

4. The transdermal administrating device according to claim 1, wherein:
said means for applying the variable bias voltage comprises a variable resistor connected between said active electrode and said inert electrode,
a material constituting said conductive electrode layer of said active electrode and said material constituting said inert electrode have different standard single electrode potentials from each other, and
said controller comprises:
a measurement circuit for measuring said internal resistance connected between said first and second conductive electrode layers in the non-dermocontact region, and
a controlling circuit for instructing said measurement circuit to measure said internal resistance, calculating a resistance value to be set onto said variable resistor based on said measured internal resistance value, and controlling said variable resistor to be at said calculated resistance value.

5. The transdermal administrating device according to claim 3, wherein:
said measurement circuit comprises standard resistors including first and second standard resistors which are different from each other, and
said measurement circuit contains both a switch for selecting which of said first and said second standard resistor is connected to the external circuit between said first and second conductive electrode layers, and a voltage meter for measuring voltages between opposite ends of said first and said second standard resistors when connected to said external circuit.

6. The transdermal administrating device according to claim 4, wherein:
said measurement circuit comprises standard resistors including first and second standard resistors which are different from each other, and
said measurement circuit contains both a switch for selecting which of said first and said second standard resistors is connected to the external circuit between said first and second conductive electrode layers, and a voltage meter for measuring a voltage between opposite ends of said first or said second standard resistor when connected to said external circuit.

7. The transdermal administrating device according to claim 1, wherein:
said dermocontact means comprises a plurality of openings and first and second sides, said active electrode, said inert electrode, said first conductive electrode layer and said second conductive electrode layer are adhered on the first side of said dermocontact means,
said controller and said bias power supply or said variable resistor are provided on the second side of said dermocontact means, and connected between said first conductive electrode layer and said second conductive electrode layer, or between said active electrode and said inert electrode through said openings.

8. The transdermal administrating device according to claim 2, wherein:
said dermocontact means comprises a plurality of openings and first and second sides,
said active electrode, said inert electrode, said first conductive electrode layer and said second conductive electrode layer are adhered on the first side of said dermocontact means,
said controller and said bias power supply or said variable resistor are provided on the second side of said dermocontact means, and connected between said first conductive electrode layer and said second conductive electrode layer, or between said active electrode and said inert electrode through said openings.

9. The transdermal administrating device according to claim 3, wherein:
said dermocontact means comprises a plurality of openings and first and second sides,
said active electrode, said inert electrode, said first conductive electrode layer and said second conductive electrode layer are adhered on the first side of said dermocontact means,
said controller and said bias power supply or said variable resistor are provided on the second side of said dermocontact means, and connected between said first conductive electrode layer and said second conductive electrode layer, or between said active electrode and said inert electrode through said openings.

10. The transdermal administrating device according to claim 1, wherein another conductive material is further coated between at least one of said first and said second conductive electrode layer and the skin.

11. The transdermal administrating device according to claim 2, wherein another conductive material is further coated between at least one of said first and said second conductive electrode layer and the skin.

12. The transdermal administrating device according to claim 3, wherein another conductive material is further coated between at least one of said first and said second conductive electrode layer and the skin.

13. The transdermal administrating device according to claim 1, wherein said active electrode acts also as said first conductive electrode layer and/or said inert electrode acts also as said second conductive electrode layer.

14. The transdermal administrating device according to claim 2, wherein said active electrode acts also as said first conductive electrode layer and/or said inert electrode acts also as said second conductive electrode layer.

15. The transdermal administrating device according to claim 3, wherein said active electrode acts also as said first conductive electrode layer and/or said inert electrode acts also as said second conductive electrode layer.

16. The transdermal administrating device according to claim 1, wherein among said materials constituting said first conductive electrode layer and said second conductive electrode layer, the material having a lower standard single electrode potential comprises an n-type semiconductor.

17. The transdermal administrating device according to claim 2, wherein among said materials constituting said first conductive electrode layer and said second conductive electrode layer, the material having a lower standard single electrode potential comprises an n-type semiconductor.

18. The transdermal administrating device according to claim 3, wherein among said materials constituting said first conductive electrode layer and said second conductive electrode layer, the material having a lower standard single electrode potential comprises an n-type semiconductor.

19. A method of transdermal administration comprising:

(a) attaching on a skin surface each of: (i) an active electrode having a conductive electrode layer and a conductive drug layer applied on one surface of said conductive electrode layer, (ii) an inert conductive electrode which is spaced from said active electrode, and (iii) a set of spaced apart conductive electrode layers each made of a material having a different standard single electrode potential, (b) detecting an electric current passing through a subcutaneous tissue between said set of conductive electrode layers, and detecting an internal resistance of said subcutaneous tissue, said internal resistance being distinct from a contact resistance and a leak resistance between the spaced apart conductive electrode layers, (c) determining said internal resistance for keeping a concentration of a delivered drug in said subcutaneous tissue at a desired level based on a predetermined calibration line representing a relationship between a concentration in blood of the delivered drug and said internal resistance, and (d) controlling said electric current passing through said active electrode, said subcutaneous tissue, and said inert electrode so as to maintain said internal resistance.

20. A transdermal administration device comprising:

a transdermal administration unit for carrying out iontophoresis, including an active electrode provided with a conductive drug layer, an inert electrode, and a variable bias voltage source for applying a variable bias voltage across said active electrode and said inert electrode;

a detection unit including a set of detection electrodes made of conductive materials having different standard single electrode potential, said detection electrodes being adapted to be brought into contact with a patient's skin at separated locations, and an external load connected to said set of detection electrodes, said external load comprising standard resistors to be alternatively connected to a circuit including said detection electrodes, a change-over switch for changing over said standard resistors, and a voltage meter for detecting voltage drops across respectively connected ones of the standard resistors;

a controller unit receiving the voltage drops and generating a control signal based on an internal resistance of a skin calculated from the voltage drops, said internal resistance being distinct from a contact resistance and a leak resistance between the detection electrodes, for controlling said variable bias voltage source.

* * * * *